US008501243B2

(12) United States Patent
Yu

(10) Patent No.: US 8,501,243 B2
(45) Date of Patent: Aug. 6, 2013

(54) TARGETING CANCER THERAPY COMBINATION

(76) Inventor: Baofa Yu, San Diego, CA (US)

(*) Notice: Subject to any disclaimer, the term of this patent is extended or adjusted under 35 U.S.C. 154(b) by 242 days.

(21) Appl. No.: 12/440,198

(22) PCT Filed: Sep. 7, 2007

(86) PCT No.: PCT/CN2007/002671
§ 371 (c)(1),
(2), (4) Date: Nov. 10, 2009

(87) PCT Pub. No.: WO2008/034346
PCT Pub. Date: Mar. 27, 2008

(65) Prior Publication Data
US 2010/0104660 A1 Apr. 29, 2010

(51) Int. Cl.
A61K 31/28 (2006.01)
A61K 33/26 (2006.01)

(52) U.S. Cl.
USPC .......................... 424/648; 514/492

(58) Field of Classification Search
USPC .......................... 424/648; 514/492
See application file for complete search history.

(56) References Cited

U.S. PATENT DOCUMENTS

| 4,160,817 | A |   | 7/1979  | Bucovaz et al. |
|-----------|---|---|---------|----------------|
| 4,447,526 | A |   | 5/1984  | Rupchock et al. |
| 4,724,230 | A |   | 2/1988  | Cone, Jr. |
| 4,832,849 | A | * | 5/1989  | Cardin ............. 210/635 |
| 4,971,991 | A |   | 11/1990 | Umemura et al. |
| 5,005,588 | A |   | 4/1991  | Rubin |
| 5,156,841 | A |   | 10/1992 | Rapp |
| 5,215,899 | A |   | 6/1993  | Dattagupta |
| 5,290,551 | A |   | 3/1994  | Berd |
| 5,340,803 | A |   | 8/1994  | Rubin |
| 5,593,900 | A |   | 1/1997  | Tryggvason et al. |
| 5,629,327 | A |   | 5/1997  | D'amato |
| 5,651,986 | A |   | 7/1997  | Brem et al. |
| 5,705,151 | A |   | 1/1998  | Dow et al. |
| 5,712,291 | A |   | 1/1998  | D'amato |
| 6,248,585 | B1 |  | 6/2001  | Berd |
| 6,811,788 | B2 | * | 11/2004 | Yu ............. 424/278.1 |
| 7,041,302 | B2 |  | 5/2006  | Roussel |
| 2005/0079133 | A1 | * | 4/2005 | Yang et al. ......... 424/1.49 |

FOREIGN PATENT DOCUMENTS

| CN | 1431909     | 7/2003  |
| EP | 240191      | 3/1987  |
| EP | 378888      | 1/1989  |
| FR | 2505182     | 11/1982 |
| JP | 11-171788   | 6/1999  |
| WO | WO 96/39226 | 12/1996 |
| WO | WO 97/11666 | 4/1997  |
| WO | WO 98/03195 | 1/1998  |
| WO | WO 98/40105 | 9/1998  |
| WO | WO 99/46385 | 9/1999  |
| WO | WO 00/06143 | 2/2000  |
| WO | WO 01/52868 | 7/2001  |
| WO | WO 03/104267 | * 12/2003 |

OTHER PUBLICATIONS

Okano et al. J. Org. Chem (1981), 46, 1138-1141.*
Auerbach, et al., "Angiogensis Inhibition: A Review" *Pharmac. Ther.* (1994) 63: 265-311.
Awwad, et al., "Modification of monoclonal antibody carbohydrates by oxidation, conjugation, or deoxymannojirimycin does not interfere with antibody effector functions" *Cancer Immunol Immunother* (1994) 38: 23-30.
Barbie, et al., "Nuclear tumor suppressors in space and time" *TRENDS in Cell Biology* (2005) 15(7): 378-385.
Coxon, et al., "Development of a Specific Polarisation Fluoroimmunoassay for Paraetamol in Serum" *Ann Clin Biochem* (1988) 25: 49-52 (Abstract Only).
Cripps, et al., "Phase II Randomized Study of ISIS 3521 and ISIS 5132 in Patients with Locally Advanced or Metastatic Colorectal Cancer: A National Cancer Institute of Canada Clinical Trails Group Study" *Clinical Cancer Research* (2002) 8: 2188-2192.
Dasgupta, Gargi and Jamil Momand, "Geldanamycin Prevents Nuclear Translocation of Mutant p53" *Experimental Cell Research* (1997) 237: 29-37.
Dieli, et al., "TCR $V_\alpha$ chain expression influences reactivity to the hapten TNP" *International Immunology* (1996) 9(1): 1-8.
Dima, et al., "Response of Murine Mammary Adenocarcinoma to Photodynamic Therapy and Immunotherapy" *Laser Ther.* (1990) 2: 153-160.
Edstrom, et al., "Mucosal Melanoma: Immunological Findings in a Rare Case Treated With BCG Vaccine, Autologous Tumor Cells, and Cytarabine" *Arch Otolaryngol* (1979) 105(1): 48-50.
Ferguson, et al., "Cell death and immune privilege" *Int. Re. Immunol.* (2002) 21(2-3): 153-172 (Abstract Only).
Gong, et al., "Differential Regulation of Sentrinized Proteins by a Novel Sentrin-specific Protease" *J. of Biological Chem.* (2000) 275(5): 3355-3359.
Hawkins, et al., "Clinical trails of antiangiogenic agents" *Current Opinion in Oncology* (1995) 7: 90-93.
Hino, et al., "Disappearance of pulmonary metastases by OK-432 treatment in a Case of Hepatocellular Carcinoma" *Acta Med Okayama* (1993) 47(4): 289-292.
Jenks, Susan, "Blocking Angiogenesis May Help Keep Tumors Dormant" *J. Natl. Cancer Institute* (1996) 88(12): 787.
Jones, et al., "Antibodies for targeted gene therapy: extracellular gene targeting and intracellular expression" *Advanced Drug Delivery Reviews* (1998) 31: 153-170.
Karzulli, et al., "N-ethylmaleimide as oxidizing agent in biological and non-biological systems" *Boll. Soc. It. Biol. Sper.* (1985) 1(LXI): 121-127.
Krosl, et al., "Potentiation of Photodynamic Therapy-elicited Antitumor Response by Localized Treatment with Granulocyte-Macrophase Colony-stimulating Factor" *Cancer Research* (1996) 56: 3281-3286.

(Continued)

*Primary Examiner* — Shirley V Gembeh
(74) *Attorney, Agent, or Firm* — Knobbe, Martens, Olson & Bear, LLP

(57) ABSTRACT

Methods for treating neoplasm, tumors and cancers, using one or more tumor treating drug carriers, haptens and anti-cancer drugs, alone or in combination with other antineoplastic agents or treatments, are provided. Also provided are compositions, and kits containing the composition for affecting the therapy.

16 Claims, 1 Drawing Sheet

(56) References Cited

OTHER PUBLICATIONS

Lin, et al., "Non-surgical treatment of hepatocellular carcinoma" *J. Gastroenterology and Hepatology* (1997) 12(Suppl.): 5319-5328.

Mansouri, Ali, "Oxidation of human hemoglobin by sodium nitrite-effect of β-93 thiol groups" *Biochem and Biophys Research Communications* (1979) 89(2): 441-447 (Abstract Only).

Marshall, et al., "A Phase II Trial of ISIS 3521 in Patients with Metastatic Colorectal Cancer" *Clin. Colo. Cancer* (2004) 4(4): 288-274.

Martin, et al., "Negative and Positive Assays of Superoxide Dismutase Based on Hematoxylin Autoxidation" *Archives of Biochem. and Biophy.* (1987) 255(2): 329-336.

O'Reilly, Michael S., "The preclinical evaluation of angiogensis inhibitors" *Investigational New Drugs* (1997) 15: 5-13.

Orkin, et al, "Report and Recommendations of the Panel to Assess the NIH Investment in Research on Gene Therapy" NIH (1995).

Oza, et al., "Phase II study of CGP 69846A (ISIS 5132) in recurrent epithelial ovarian cancer: an NCIC clinical trials group study (NCIC IND.116)" *Gyn. Oncology* (2003) 89: 129-133.

Rudnic, E., "Oral Solid Dosage Forms" in: Remington's Pharmaceutical Sciences, $18^{th}$ Ed., 1990, pp. 1633-1665.

Santini, et al., "The Oxidizing Agent Menadione Induces as Increase in the Intracellular Molecular Oxygen Concentration in K562 and A431 Cells: Direct Measurement Using the New Paramagnetic EPR Probe Fusinite" *Free Radical Biology & Medicine* (1996) 20(7): 915-924.

Schneider, et al., "Development of a new class of replicating viral vectors for cytolytic gene therapy" *Gene Ther.* (1999) 6(Suppl.): S5 (Abstract Only).

Skobelkin, et al., "Preoperative Activation of the Immune System by Low Reactive Level Laser Therapy (LLLT) in Oncologic Patients: A Preliminary Report" *Laser Therapy* (1991) 3(4): 169-176.

Todryk, et al., "Heat Shock Protein 70 Induced During Tumor Cell Killing Induces Th1 Cytokines and Targets Immature Dendritic Cell Precursors to Enhance Antigen Uptake" *J. Immunology* (1999) 163: 1398-1408.

Tolcher, et al., "A Randomized Phase II and Pharmacokinetic Study of the Antisense Oligonucleotides ISIS 3521 and ISIS 5132 in Patients with Hormone-refractory Prostate Cancer" *Clin. Cancer Research* (2002) 2530(2): 2530-2535.

Uehara, Y., "Protein kinase inhibitors—Screening of a new molecular target therapeutics" *Cancer & Chemotherapy* (1997) 24(2): 136-144 (Abstract Only).

Verma, et al., "Gene therapy—promises, problems and prospects" *Nature* (1997) 389: 239-242.

Yumita, et al., "The Increase of Generation of Superoxide Radicals and the Inhibitory Effect on Yoshida Sarcoma of Anthracycline Antitumor Agents by Ultrasound" *J. Japan Society for Cancer Therapy* (1989) 24(1): 63-68. (English Summary Only).

Zhang, et a., "Effect of radiation and tirapazamine (SR-4233) on three melanoma cell lines" *Mel. Research* (1998) 8: 510-515.

*Advanced Inorganic Chemistry: A Comprehensive Text*, F. Albert Cotton and Geoffrey Wilkinson $3^{rd}$ Ed., 1972, p. 408.

*Drug Facts and Comparisons*, T. Burnham Ed., 2000, p. 1807.

*Fundamental Immunology*, William E. Paul, MD $3^{rd}$ Ed., 1993, 1157-1170.

*Glossary of Genetics: Classical and Molecular*, Rieger, et al. $5^{th}$ Ed., 1991, p. 422.

*Goodman & Gilman's The Pharmacological Basis of Therapeutics*, $9^{th}$ Ed., Stephen L. Eck and James M. Wilson (1996), Chapter 5, pp. 77-101.

*Protein Engineering of Antibody Molecules for Prophylactic and Therapeutic Applications in Man*, Mike Clark Ed., 1993, p. 4-5.

*Remington: The Science and Practice of Pharmacy*, vol. 1, Chapter 38: Stability of Pharmaceutical Products, Elizabeth B. Vodas, Ph.D., $19^{th}$ ed., 1995.

MeSH Term Invormaiton, *NLM Gateway*, from http://gateway.nlm.nih.gov/gw/Cmd?linkVars=SessionID%3D080526180415458006153610 . . . , obtained on May 26, 2008.

International Search Report dated Dec. 6, 2007, issued in International Application No. PCT/CN2007/002671.

*SIGMA: Biochemicals and Reagents for Life Science Research*, (1999) p. 2399.

\* cited by examiner

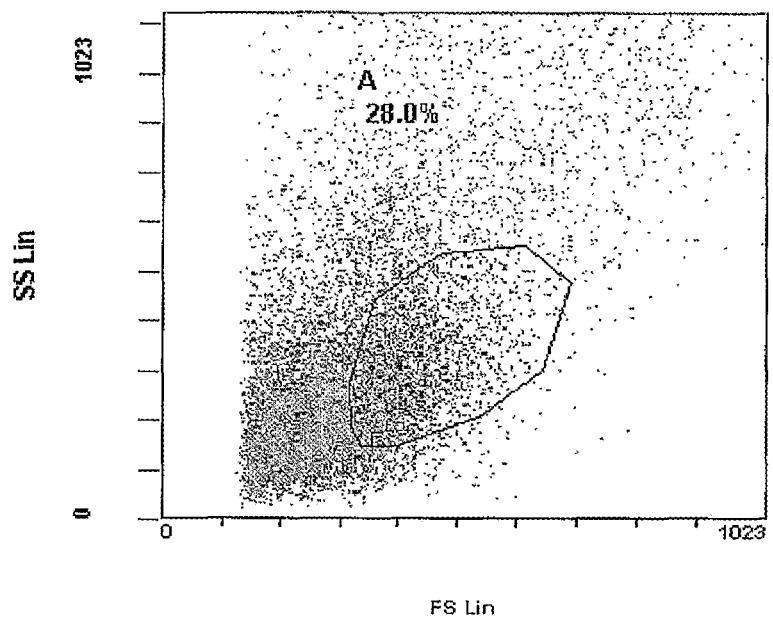
[F1][Ungated] 2.LMD : FS Lin/SS Lin - ADC
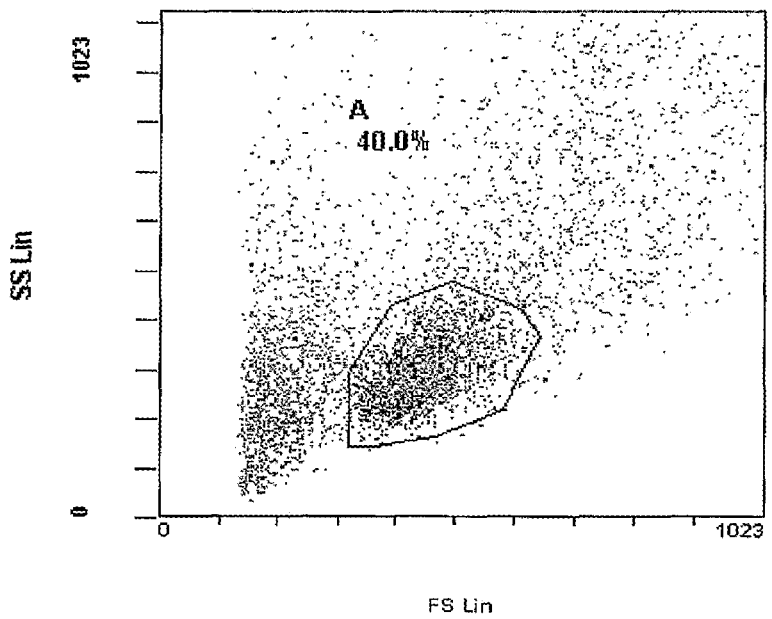

TARGETING CANCER THERAPY COMBINATION

RELATED APPLICATIONS

This application is a U.S. National Phase of International Application No. PCT/CN2007/002671, filed Sep. 7, 2007, designating the U.S. and published on Mar. 27, 2008 as WO 2008/034346, which claims priority to Chinese Patent Application No. 200610151437.0, filed Sep. 7, 2006. The content of these applications is incorporated herein by reference in its entirety.

BACKGROUND OF THE INVENTION

1. Field of the Invention

The present invention relates to compositions and methods for treating neoplasms in mammals, particularly human. More particularly, combinations for intravenous administration of tumor agents comprising targeting compound, anticancer drugs and agents that enhance the inflammatory response are provided, an intravenous route of the only effective route of administration for treatment. Also provided are methods for treating neoplasms by administration of the combinations.

2. Description of the Related Art

A number of approaches, including surgery, chemotherapy and radiation, to cancer therapy have been used. Surgery is a traditional approach in which all or part of a tumor is removed from the body. Surgery generally is only effective for treating the earlier stages of cancer. However, for more than 50% of cancer patients by the time they are diagnosed, they are no longer candidates for effective surgical treatment. Surgical procedures may increase tumor metastases through blood circulation during of the surgery procedure. Most of cancer patients do not die from the cancer at the time of diagnosis or surgery, but rather die from the metastasis and the recurrence of the cancer.

Other therapies are also often ineffective. Radiation therapy is only effective for local cancer therapy at early and middle stages of cancer, and is not effective for the late stages of cancer with metastasis. Chemotherapy can be an effective method, which is commonly used, but there are severe side effects, e.g., vomiting, low white blood cells (WBC), loss of hair, loss of weight and other toxic effects. Because of the extremely toxic side effects, many cancer patients cannot successfully finish a complete chemotherapy regimen. A considerable number of cancer patients die from the chemotherapy due to poor tolerance to the toxic side effects of chemotherapy. The extreme side effects of anticancer drugs are caused by the poor target specificity of such drugs. The drugs reach most normal organs of patients as well as intended target tumors through circulation. Meanwhile, the poor target specificity wherein only a small fraction of the drugs is correctly targeted and a majority of drugs acts on non-targeted tissues causes side effects also decreases the efficacy of chemotherapy because. The efficacy of chemotherapy is further decreased by poor retention of the anticancer drugs within the target tumors. Accordingly, enhancing the target specificity of drugs is one solution to increase the retention behavior of drugs within tumors and the specified local tumor killing.

Immunotherapy, including the use of cancer vaccines, such as autologous vaccines, is effective for cancer patients with tumor burdens of less than $10^8$ tumor cells. Immunotherapy is often used as an adjunctive therapy in combination with other therapies such as surgery, radiation therapy and chemotherapy to clean out any remaining tumor cells from the body. Immunotherapy and the use of tumor vaccines have not proven effective against a tumor burden greater than $5 \times 10^9$ to $10^{11}$ tumor cells, which is typical in a patient with small, symptomatic metastases. In addition, autologous tumor vaccination involves complicated procedures and requires a tumor specimen be processed for each patient to be treated, thus it is not capable to fulfill the needs of patients.

At present, there is no effective treatment for patients with late stage tumors. Since earlier stage tumors are not easily detectable, many patients who are diagnosed with cancer are at the later stages of cancer with the tumor burden greater than $5 \times 10^9$ to $10^{11}$ tumor cells, or the tumor has already metastasized into other tissues. For these patients, traditional cancer therapies such as surgery, radiation therapy and chemotherapy may no longer be effective and/or suitable.

A series of compounds have been found laboratorially and clinically to have the specificity of tumor targeting. Some of them have been utilized in clinical tumor imaging and therapy. However, the targeting drugs used for treatments are chosen mostly from radioisotopes, and the effect is still limited to pain killing, which is not capable to achieve partial or complete alleviation. Currently treatments of tumors still emphasize comprehensive therapy, especially by combination of immunotherapy and chemotherapy, which have been proven theoretically to be the best partners in clinical practices, even certain immunological effects achieved by chemotherapy.

Despite some progress of cancer therapy, there are few, if any, effective treatments. Due to the severity and breadth of late stage cancer towards life, there is a great clinical need for effective treatments of such diseases or disorders. The desired cancer therapy is one that treats primary tumors by targeting carrier delivery of drugs and meanwhile stimulates the autologous immunological competence in human body to eradicate systemic small tumors at multiple sites in the body, and that discriminates specifically between neoplastic and non-neoplastic cells, thus achieving the treatment and prevention of the tumor metastasis.

Accordingly, it is an object of the present invention to provide a method for such cancer therapy. In particular, it is an object of the present invention to provide a carrier targeting therapy which treats primary tumors or systemic tumors and meanwhile stimulates the autologous immunological competence within human body to eradicate systemic small tumors at multiple sites in the body, and which discriminates specifically between neoplastic and non-neoplastic cells, thus achieving the treatment and prevention of the tumor metastasis.

The present invention differs from the previous invention of the Applicant (Chinese Patent Application No. 01806830.8, Publication No. CN1431909A, published on Jul. 23, 2003.):

1. The present invention mainly relates to a method of tumor therapy by intravenous administration, while the previous invention relates to a method of tumor therapy by intratumoral administrations;

2. The present invention relates to an integration of carrier drug(s) and adjuvant(s), which may be a conjugate or in other joined forms, while the previous invention is directed to a composition of some compounds, which may not be a conjugate;

3. The conjugate of the invention, wherein the carrier still functions to deliver drugs to targeted sites (tumors or organs where tumors locate), and the drug(s) and adjuvant(s) function independently to achieve the purpose of treatment, while the previous invention only relates to a composition of some compounds without carrying or targeting effects, wherein such combination only acts within local tumors;

4. The reduce agent of the present invention functions only when the conjugate is formed, and is not involved in the action of tumor therapy, while the reduce agent of the previous invention functions during the formation of sustained released drugs within tumors, and also functions to directly kill tumor cells;

5. The present invention relates to a method of systemic therapy, which can directly treat tumors located in more than one sites, while the previous invention only relates to a method of local therapy, which can only treat local tumors;

6. The present invention is consistent with the previous one in that the inflammatory response and immunological response of the treated tumors are the same, which may results in antibodies against tumor and lymphocytes with cytotoxicity that function to kill and wound tumors.

SUMMARY OF THE INVENTION

In the present invention, a conjugate is formed by combining chemotherapy with immunotherapy via carriers, and the chemotherapeutic drug and immunological adjuvant are simultaneously administrated intravenously to the site of the tumor. A conjugate is formed by a non-covalent bond based self-assembly chemical complex materials. When the chemotherapeutic drug acts to kill the tumor, the immunological adjuvant functions to modify the products of tumor desintegration or proteins resulting from tumor degradation into products which can be recognized by immunocytes to produces immune response when presented by major histocompatibility complex (MHC), thus achieving the immunological effect as tumor-specific immunizing antigens. The present invention relates to enhancing tumor immunogenicity, which results in immunotherapy, so that the anticancer effect is enhanced and the dosage and side effects of chemotherapy are reduced. Accordingly, the deficiencies of chemotherapy are complemented, wherein the probability of relapse may be reduced or the metastases may be prevented, even the small tumor metastasis may be treated.

DETAILED DESCRIPTION OF THE PREFERRED EMBODIMENT

The present invention mainly uses a conjugate composed of a redox agent such as stannous chloride ($SnCl_2$), a neoplasm-targeting compound such as Methylene Diphosphonate Injection (MDP), an anticancer agent such as Ara-C, and an immunologic adjuvant DNP. The bone-seeking property of MDP permits effective delivery of the MDP-Ara-C-DNP conjugate to the bone tumor tissue where the anticancer agent Ara-C exerts anticancer effects and the DNP functions as an immunologic adjuvant to modify the antigens from the lysis of tumor killed by anti-cancer drug.

The invention provides a combination to be used via intravenous administration for treating, which comprises an agent targeting tumor tissues, an agent effective in killing tumor tissues and an agent capable of enhancing inflammatory response against the tumor left by the chemotherapy. Preferred among these combinations are those comprising the three components for intravenous injection to treat tumor, and method of using them in treatment. The combinations comprise an oxidizing agent or a reducing agent, a tumor tissue-targeting agent or anticancer drugs, and a hapten. These combinations are used to treat tumors, such as a solid tumor.

As shown herein, these combinations, such as those comprising one or more oxidizing and/or reducing agents, tumor tissue-targeting agents, anticancer drugs and hapten, are highly applicable in the treatment of various neoplasms, tumors and cancers, especially solid tumors that are not effectively treatable with traditional cancer therapies such as surgery, radiotherapy, and immunotherapy.

Provided herein are methods and combinations for treating malignant neoplasms, tumors and cancers. Encompassed within the methods are the uses of any combinations of one or more oxidizing agents or reducing agents, tumor tissue-targeting agents, anticancer drugs and haptens, which can alleviate, reduce, ameliorate, or prevent neoplasms, tumors and cancers; or place or maintain in a state of remission of clinical symptoms or diagnostic markers associated with such neoplasms, tumors and cancers, particularly solid tumors that are not effectively treatable with traditional cancer therapy such as surgery, radiation therapy, chemotherapy and immunotherapy. The combinations can be used alone or in conjunction with other treatments for neoplasms, tumors and cancers.

The neoplasms, tumors and cancers that can be treated include, but are not limited to, the neoplasm of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasm, lymph and lymph node metastases of various cancers, and malignant lymphoma. Preferably, the neoplasms, tumors and cancers to be treated are a solid tumor. The combinations are particularly effective for solid tumors, including solid tumor larger than $10^8$ cells, e.g., from about $5 \times 10^9$ to about $10^{11}$ cells but not limited to other kind of any size tumors.

The combinations provided herein improve the therapeutic efficiencies of cancer therapy for cancer patients, including earlier stage cancer patients having visible tumor mass and being unsuitable as candidates for surgery, as well as late-stage cancer patients with larger tumors or metastases for whom the opportunity for surgery may have passed.

Each component may be a separate composition or agent, or may be combined. Before using, each component has to be conjugated as a complex for intravenous delivery to tumor side for function. If each component of chemical carrier/targeting agent, anticancer drugs and hapten alone with systemic intravenous administration, it would not be effective for targeting kill of tumors and induce the immunological effect. The combination is intended to induce killing of the neoplasm and to enhance the inflammatory response to the necrotic tumor tissue.

Therefore, the combinations provided herein are preferably in the form of pharmaceutical compositions, including compositions of one or more oxidizing agents or reducing agents, tumor tissue-targeting agents, antitumor chemical drugs and haptens. The combinations are typically pharmaceutical compositions that include an oxidizing agent or reducing agent, a tumor tissue-targeting agent, an anticancer preparation, and a hapten formulated for single dosage administration. The targeting compound must be conjugated with anticancer drug and/or hapten for a complex. The compound anticancer drug and hapten can be administered separately for a conjugate with targeting carrier, such as successively, or can be administered intermittently, or together as three separate compositions as a mixture in a single composition. When each complex administered successively or intermittently, the time period between administrations of each is typically on the order of less than a day, preferably less than an hour, but may be longer. The precise order and timing of administration can be determined empirically.

The dosage of each combination can be empirically determined, but is generally the dosage normally used for treating neoplasms, tumors and cancers, and an amount sufficient to further enhance other neoplasm treatment, or sufficient when used alone to reduce or ameliorate or in some manner reduce symptoms of the neoplasms. The combinations can be packaged as kits.

Immunologic adjuvants can also be incorporated in the combinations. Such adjuvants include, but are not limited to, hapten. Bacille-Calmette-Guerin (BCG), interferons or the colony-stimulating factor GM-CSF pre-treated with low dose cyclophosphamide.

When the combination is administered to form a carrier targeting therapy, which through the anticancer drug directly kills a large number of tumor cells, resulting in the shrinking of the neoplasm. This leads to a lower tumor burden, which allow immunotherapy or tumor vaccine treatment to take effect. It also creates an area of inflammation that attracts lymphocytes and other inflammatory response mediators to the target tumor site. The attracted lymphocytes include the tumor antigen presenting cells (APCs), macrophages, dendritic cells (DCs), and activated B cells. These lymphocytes are exposed to tumor antigens generated from the tumor cell lysis and elicit a tumor-specific immune response.

When inflammation and tumor cell lyses ensue after an target therapy is administered, the lysis tumor cells killed by anticancer drug in the target area of tumor are modified with the haptens, resulting in modified, MHC-associated peptides with more complex immunogens, which are then released to function as an autologous tumor vaccine. Such a tumor vaccine enhances the patient's own tumor immunogenicity, and stimulates T lymphocytes against the live tumor cells in and around the original tumor that are not killed, metastasized tumor and micro-lesions of tumor. Such an autologous tumor vaccine likely plays an important role in the prevention of the tumor metastases and recurrences of tumor.

The combinations can also include other agents, such as anti-angiogenic agents, radiosensitizers and other cancer therapeutics. For example, a conjugate can also be formed through combination, which slowly releases an antiangiogenic agent to inhibit the blood microvessel formation that is needed for new tumor growth.

The anti-neoplastic (anti-cancer) agents used in the combinations and methods include, but are not limited to, an anti-angiogenic agent, an alkylating agent, an antimetabolite, a natural product, a platinum coordination complex, an anthracenedione, a substituted urea, a methylhydrazine derivative, an adrenocortical suppressant, a hormone and an antagonist, an oncogene inhibitor such as an anti-oncogene antibody or an antioncogene antisense oligonucleotide, an anti-cancer polysaccharide, or herb extracts such as Chinese herb extracts.

In one embodiment, the combination contains a single composition containing one or more oxidizing agents and/or reducing agents, tumor tissue-targeting agents, anticancer preparations and haptens formulated for injectable delivery; or four compositions with one containing an oxidizing agent or a reducing agent, another one containing a tumor tissue-targeting agent and an anticancer agent, and still another one containing a hapten, wherein each one is in a pharmaceutically acceptable carrier or excipient in an injectable form. Specific therapeutic regimens, pharmaceutical compositions, and kits are also provided.

In a specific embodiment, a combination is provided, which combination comprises: a) a tissue-targeting agent; and b) an anti-neoplastic (anticancer) agent, such as Ara-C. In addition, a combination is provided which contains a) an oxidizing agent or a reducing agent; b) a tissue-targeting agent; c) an anti-neoplastic (anticancer) agent, such as Ara-C; and d) a hapten DNP or TNP.

In a specific embodiment, a combination is provided which comprises: a) an oxidizing agent or a reducing agent; and b) an anti-neoplastic (anticancer) agent, such as Ara-C.

In another specific embodiment, a combination is provided which comprises: a) a hapten; and b) a tissue-targeting agent.

In still another specific embodiment, a combination is provided which comprises: a) a hapten; and b) an oxidizing agent or a reducing agent.

Also provided is a method for treating neoplasm, especially solid tumors, in a mammal preferably a human, comprising in situ administration of an effective amount of a hapten and therapeutic agent(s) that causes inflammatory necrosis of the neoplasm, whereby an autologous immune response is generated against the neoplasm and the neoplasm is treated. The autologous immune response generated against the neoplasm can be a humoral and/or a cellular immune response.

Haptens used in the treatment include, but are not limited to, trinitrophenol (TNP), dinitrophenol (DNP), N-iodoacetyl-N'-(5-sulfonic 1-naphtyl)ethylene diamine (AED), dinitrofluorobenzene (DNFB).

The oxidizing agents and compositions used in the method and combination include, but not limited to, stannous chloride ($SnCl_2$), stannous sulfate ($SnSO_4$) stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate (SnS3), and stannous sulfide (SnS).

Reducing agents used in the combinations and methods include, but are not limited to, hematoxylin, a hypoxic reducing agent such as a nitroimidazole, and nonnitro compound SR 4233.

The tissue-targeting agents used in the combinations and treatments herein include, but not limited to, Sodium Dimercaptosuccinate (III) (DMSA-III), Sodium Dimercaptosuccinate (V) (DMSA-V), Sodium Pyrophosphate and Stannous Chloride for Injection (PYP), Methylene Diphosphonate for Injection (MDP), Tetrofosmin, polymerized albumin, Mercaptoacetyltriglycine, Pentetic Acid and Stannous Chloride (DTPA), Sodium Glucoheptonate and Stannous Chloride, L, L-Ethyl Cysteinate Dimer and Stannous Chloride (ECD), Exametazime (HMPAO), Etifenin and Stannous Chloride, Sodium Phytate and Stannous Chloride, $Cu(MIBI)_4BF_4$ (MIBI), α-methyltyrosine, MIBI (2-methoxy isobutyl isonitrile), 2-nitroimidazole, monoclonal antibodies and monoclonal antibodies against neoplasm, and traditional Chinese drug extracts such as Bruceantin, Tetrandrine, thalicarpine, maytansine, etc., see Table 1.

TABLE 1

| | Tumor targeting agents | Targeting organs |
|---|---|---|
| 1 | Methylene Diphosphonate for Injection (MDP) | Bone and bone tumor, bone metastasis |
| 2 | Sodium Pyrophosphate and Stannous Chloride for Injection (PYP) | Bone system |
| 3 | Pentetic Acid and Stannous Chloride (DTPA) | Kidney |
| 4 | Sodium Dimercaptosuccinate (III) (DMSA-III) | Kidney |
| 5 | Sodium Dimercaptosuccinate (V) (DMSA-V) | Soft tissue tumor |
| 6 | Tetrofosmin | Tumor |

TABLE 1-continued

| Tumor targeting agents | Targeting organs |
| --- | --- |
| 7  Bis (N-ethoxy-N-ethyl dithiocarbamato) nitrido (NOET) | Tumor |
| 8  L-Ethyl Cysteinate Dimer and Stannous Chloride for Injection (ECD) | Brain |
| 9  Exametazime Injection | Brain |
| 10 Albumin A aggregated and Stannous chloride for injection (MAA KIT) | Lung |
| 11 Sodium Phytate and Stahnous Chloride for Injection. (PHY) | Liver |
| 12 Etifenin and Stannous Chloride for Injection (EHIDA) | Liver and gallbladder |
| 13 Bruceantin, Tetrandrine, thalicarpine, maytansine | Lymph system |
| 14 2-Nitroimidazole | Tumor hypoxia |
| 15 Tumor antibodies | Tumor |

Preferably, said combination also includes a facilitating agent and said method further comprises administering a facilitating agent that facilitates conjugation between the hapten and a tumor antigen of the neoplasm. The facilitating agents include, but are not limited to, a chelator such as glycyltyrosyl-(N-e-diethylenetriaminepetaacetic acid)-lysine (GYK-DTPA) or doxorubicin adipic-dihydrazide (ADR-ADH), or a chemical linking agent such as carbodimide.

Also preferably, the combination also includes an immune response potentiator, and further comprises methods for administering an immune response potentiator to the neoplasm. The immune response potentiators include, but are not limited to, polysaccharides, herb extracts such as Chinese herb extracts, Bacille Cahnette-Guerin (BCG), *Corynebacterium Parvum*, an enzyme such as *Vibrio cholera* neuraminidase (VCN), Papain, B-Gal and ConA.

These combinations and methods can also be administered simultaneously, successively or in conjunction with chemotherapy, e.g., by further including two or more anti-neoplasm agents in the combination of tissue-targeting agents, or administering a combination provided herein, and then administering a chemotherapy in conjunction there with, preferably within the same day, week or other cycle.

In a preferred embodiment, a particular combination is used in treatment comprising stannous chloride as oxidizing agent, MDP as agent targeting bone tissues, Ara-C as anticancer agent and DNP as hapten, to be adminstered to treat osteocarcinoma and osseous metastases of malignant tumors. After the conjugate of MDP, ARA-C and DNP formed by stanous chloride of the oxidizing agent, the conjugate is delivered to bone area, special tumor area of bone, Ara-C and DNP will be higher concentration in tumor of bone than other organs by this targeting delivery, and Ara-C and DNP will depart from this complex in tumor of bone, and Ara-C will kill the tumor in the bone by MDP delivered, and DNP in tumor area of bone will modified the lysis of tumor killed by chemical drug, further stimulate the immunological response to tumor and it resulted in the better of tumor shrinkage and longer life of patients. Composition of the invention that is not achieved by the administration of one or more of the components alone.

In another preferred embodiment, the oxidizing agent or reducing agent used is from about 0.01% (w/w) to about 35% (w/w), used is from about 1% (w/w) to about 98% (w/w) and the hapten used is from about 1 mg/ml to about 80 mg/ml.

In a preferred embodiment, the hapten, the anticancer agent, and the tissue-targeting agent are administered to the neoplasm via intravenous injection or intratumoral injection In a preferred embodiment, the hapten, the anticancer agent, and the tissue-targeting agent are administered to the neoplasm in conjugated complex with a surgical procedure.

Further provided is a method for treating neoplasm, in particular solid tumors, in a mammal preferably a human, comprising in situ administration of an effective amount of an anti-neoplastic (anti-cancer) agent, such as Ara-C, and tissue-targeting agent(s) or therapeutic agent(s) that targets to the tissues of the neoplasm, whereby the neoplasm is treated. Preferably, the tissue-targeting agent is a protein preparation or a compound, protein preparation may be antitumor antibodies and a chemical compound such as MDP which targeting to bone tumors.

In another particular embodiment is provided a method for treating neoplasm, in particular solid tumors, in a mammal preferably a human, comprising administering in situ an effective amount of an anti-neoplastic (anticancer) agent, such as Ara-C, a redox agent, and Sodium Dimercaptosuccinate V (DMSA-V) as a tumor tissue-targeting agent which is capable of reaching a soft connective tissue tumor, whereby a soft connective tissue tumor is treated.

In another particular embodiment is provided a method for treating neoplasm, in particular solid tumors, in a mammal preferably a human, comprising administering in situ an effective amount of an anti-neoplastic (anticancer) agent, such as Ara-C, a redox agent, DNP as an immunologic adjuvant, and Pentetic Acid and Stannous Chloride (DTPA) as a tumor tissue-targeting agent which is capable of reaching a renal neoplasm, whereby a renal tissue neoplasm is treated, further DNP modified the debris of tumor and stimulate the immunological response to micrometastasis.

In another particular embodiment is provided a method for treating neoplasm, in particular solid tumors, in a mammal preferably a human, comprising administering in situ an effective amount of an anti-neoplastic (anticancer) agent, such as Ara-C, a redox agent, DNP as an immunologic adjuvant, and NOET as a tumor tissue-targeting agent which is capable of reaching a tumor tissue, whereby a neoplasm is treated and DNP modified the lysis of tumor killed by the anticancer agent.

In another particular embodiment is provided a method for treating neoplasm, in particular solid tumors, in a mammal preferably a human, comprising administering in situ an effective amount of an anti-neoplastic (anticancer) agent, such as DDP, a redox agent, DNP as an immunologic adjuvant, and PHY as a hepatic tissue- (or lymph-) targeting agent which is capable of reaching a tumor tissue, whereby a hepatic neoplasm (or a malignant neoplasm in the lymphatic system) is treated, further DNP modified the lysis of tumor killed by the anticancer agent.

In another particular embodiment is provided a method for treating neoplasm, in particular solid tumors, in a mammal preferably a human, comprising administering in situ an effective amount of an anti-neoplastic (anticancer) agent, such as Ara-C, a redox agent, DNP as an immunologic adjuvant, and EHIDA as a hepatobiliary system-targeting agent which is capable of reaching a hepatobiliary tissue, whereby a malignant neoplasm in the hepatobiliary system is treated, further DNP modified the lysis of tumor killed by the anticancer agent, whereby an autologous immune response is generated against the neoplasm and the neoplasm is treated.

In another particular embodiment is provided a method for treating neoplasm, in particular solid tumors, in a mammal preferably a human, comprising administering in situ an effective amount of an anti-neoplastic (anticancer) agent, such as Ara-C, a redox agent, DNP as an immunologic adjuvant, and ECD as a brain-targeting agent which is capable of reaching a brain tissue, whereby a malignant neoplasm in the brain system is treated, further DNP modified the lysis of tumor killed by the anticancer agent, whereby an autologous immune response is generated against the neoplasm and the neoplasm is treated.

In yet another specific embodiment, a method is provided for treating neoplasm, in particular solid tumors, in a mammal preferably a human, which method comprises in situ administration of an effective amount of a hapten, a tissue-targeting agent and an anticancer agent, whereby the anticancer agent and hapten were delivered to tumor, whereby an autologous immune response is generated against the neoplasm and the neoplasm is treated.

In yet another specific embodiment, a method is provided for treating neoplasm, in particular solid tumors, in a mammal preferably a human, which method comprises in situ administration of an effective amount of a hapten and an oxidizing agent or a reducing agent, whereby an autologous immune response is generated against the neoplasm and the neoplasm is treated.

The invention provides a combination which comprises: a) redox agent (an oxidizing agent or a reducing agent); b) one or more targeting compounds; and c) one or more chemical drugs.

In an embodiment of the invention, the redox agent, targeting compound and chemical drug are formulated in a single pharmaceutical composition, or each is formulated in a separate pharmaceutical composition.

In an embodiment of the invention, the redox agent is selected from the group consisting of stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS).

In an embodiment of the invention, the reducing agent is selected from the group consisting of a hypoxic reducing agent and nonnitro compound tirapazamine (SR-4233).

In an embodiment of the invention, the hypoxic reducing agent is a nitroimidazole.

In an embodiment of the invention, the targeting compound is selected from the group consisting of any carrier capable of delivering an agent to a targeted tissue, Sodium Dimercaptosuccinate (III) (DMSA-III), Sodium Dimercaptosuccinate (V) (DMSA-V), Sodium Pyrophosphate and Stannous Chloride for Injection (PYP), Methylene Diphosphonate for Injection (MDP), polymerized albumin, Mercaptoacetyltriglycine, Pentetic Acid and Stannous Chloride (DTPA), Sodium Glucoheptonate and Stannous Chloride, L, L-Ethyl Cysteinate Dimer and Stannous Chloride (ECD), Exametazime (HMPAO), Etifenin and Stannous Chloride, Sodium Phytate and Stannous Chloride, $Cu(MIBI)_4BF_4$ (MIBI), α-methyltyrosine, MIBI (2-methoxy isobutyl isonitrile), 2-nitroimidazole, monoclonal antibodies and monoclonal antibodies against neoplasm, and traditional Chinese drug extracts such as Bruceantin, Tetrandrine, thalicarpine, maytansine, etc such as from Table 1.

In an embodiment of the invention, the chemical drug is any drug useful in treating cancer, cisplatin, carboplatin, calcium folinate, vincristine, methotrexate, fluorouracil, Ara-C, cyclophosphamide, epirubicin, doxorubicin rapid dissolution, mitomycin, etoposide, bleomycin A5, etc.

In an embodiment of the invention, the chemical drug is selected from the group consisting of hapten trinitrophenol (TNP), dinitrophenol (DNP), N-iodoacetyl-N'-(5-sulfonic 1-naphtyl)ethylene diamine (AED), dinitrofluorobenzene (DNFB).

In an embodiment of the invention, the combination further comprises an anti-neoplasm agent.

In an embodiment of the invention, the anti-neoplasm agent in the combination is an antiangiogenic agent.

In an embodiment of the invention, the anti-angiogenic agent is selected from the group consisting of an inhibitor of basement membrane degradation, an inhibitor of cell migration, an inhibitor of endothelial cell proliferation, and an inhibitor of three-dimensional organization and establishment of potency.

In an embodiment of the invention, the anti-neoplasm agent is selected from the group consisting of an alkylating agent, an antimetabolite, a natural product, a platinum coordination complex, an anthracenedione, a substituted urea, a methylhydrazine derivative, an adrenocortical suppressant, a hormone, an antagonist, an anti-cancer polysaccharide, and an herb extract, such as a traditional Chinese drug extract.

In an embodiment of the invention, the anti-neoplasm agent is an oncogene inhibitor or a tumor suppressor gene or protein.

In an embodiment of the invention, the oncogene inhibitor is an antioncogene antibody or an anti-oncogene antisense oligonucleotide.

In an embodiment of the invention, the combination further comprises a facilitating agent that facilitates conjugation between the chemical drug and the targeting agent.

In an embodiment of the invention, the facilitating agent is a chelator or a chemical linking agent.

In an embodiment of the invention, the chelator is glycyl-tyrosyl-(N-e-diethylenetriaminepentaacetic acid)-lysine (GYK-DTPA) or doxorubicin adipic dihydrazide (ADR-ADH).

In the embodiment of this invention, all of components mixed and conjugated to a complex by non-covalent in the ampoule of mixture at room temperature before the intravenous injection.

In an embodiment of the invention, the chemical linking agent is carbodimide.

In an embodiment of the invention, the combination further comprises an immune response potentiator.

In an embodiment of the invention, the immune response potentiator is selected from the group consisting of Bacille Calmette-Guerin (BCG), *Corynebacterium Parvum, Brucella abortus*, glucan, levamisole, tilorone, an enzyme and a nonvirulent virus.

In an embodiment of the invention, the redox agent in the combination is $SnCl_2$ and the targeting compound is any organ- or neoplasm-targeting compound.

In an embodiment of the invention, the redox agent in the combination is $SnCl_2$ and the chemical drug is any compound having anticancer effects.

In an embodiment of the invention, the redox agent such as SnCl2 in the combination is from about 0.01% (w/w) to about 35% (w/w), the targeting compound such as MDP is used at from about 1% (w/w) to about 98% (w/w), and the chemical drug such as ARA-C is used at from about 1 mg/ml to about 80 mg/ml. An embodiment of the invention provides a kit comprising a combination, which combination comprises: a) redox agent (an oxidizing agent or a reducing agent); b) a targeting compound; and c) a chemical drug.

An embodiment of the invention provides an article of manufacture comprising: a) packaging material; b) the above-described combination; and c) a label indicating that the article is for treating neoplasms. When it is ready to use, add chemical drugs to targeting agent such as MDP for 2 minutes then dilute it into 250 physiological normal saline for intravenous drops. Or at same time add DNP into targeting agent such as MDP for same intravenous drops for three times per week in totally 4 weeks.

Also provided herein is the use of an effective amount of a combined therapeutic agent in the preparation of a medicament for treating neoplasm in a mammal. Each chemical drug and targeting agent and hapten should be 10 mg to 50 mg in 10 to 50 ml normal saline for forming the conjugate. After conjugate formed 1 to 5 minutes, then dilute it into 250 physiological normal saline for intravenous drops.

In an embodiment the combined therapeutic agent comprises a) a redox agent (an oxidizing agent or a reducing agent); b) a targeting compound; and c) a chemical drug.

In a use according to the invention, said mammal is human.

In a use according to the invention, the targeting compound is selected from the group consisting of Sodium Dimercaptosuccinate (III) (DMSA-III), Sodium Dimercaptosuccinate (V) (DMSA-V), Sodium Pyrophosphate and Stannous Chloride for Injection (PYP), Methylene Diphosphonate for Injection (MDP), polymerized albumin, Mercaptoacetyltriglycine, Pentetic Acid and Stannous Chloride (DTPA), Sodium Glucoheptonate and Stannous Chloride, L, L-Ethyl Cysteinate Dimer and Stannous Chloride (ECD), Exametazime (HMPAO), Etifenin and Stannous Chloride, Sodium Phytate and Stannous Chloride, $Cu(MIBI)_4BF_4$ (MIBI), α-methyltyrosine, MIBI (2-methoxy isobutyl isonitrile), 2-nitroimidazole, monoclonal antibodies and monoclonal antibodies against neoplasm, and traditional Chinese drug extracts such as Bruceantin, Tetrandrine, thalicarpine, maytansine, etc such as from table 1.

In a use according to the invention, the chemical drug is selected from the group consisting of any drug useful in treating cancer, cisplatin, carboplatin, calcium folinate, vincristine, methotrexate, fluorouracil, Ara-C, cyclophosphamide, epirubicin, doxorubicin rapid dissolution, mitomycin, etoposide, bleomycin A5, etc.

In a use according to the invention, the chemical drug is selected from the group consisting of trinitrophenol (TNP), dinitrophenol (DNP), N-iodoacetyl-N'-(5-sulfonic 1-naphtyl)ethylene diamine (AED), dinitrofluorobenzene (DNFB).

In a use according to the invention, the redox agent is selected from the group consisting of stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS).

In a use according to the invention, the redox agent can also be a chelator, which is glycyltyrosyl-(N-e-diethylenetriaminepetaacetic acid)-lysine (GYK-DTPA) or doxorubicin adipic-dihydrazide (ADR-ADH).

In a use according to the invention, the redox agent can also be a chemical linking agent, which is carbodimide.

In a use according to the invention, the use further comprises using an immune response potentiator.

In a use according to the invention, the immune response potentiator is selected from the group consisting of Bacille Calmette-Guerin (BCG), *Corynebacterium Parvum*, *Brucella abortus* extract, glucan, levamisole, tilorone, an enzyme, a nonvirulent virus, a polysaccharide, and an herb extract.

In a use according to the invention, the enzyme is selected from the group consisting of *Vibrio cholera* neuraminidase (VCN), Papain, 13-Gal and ConA.

In a use according to the invention, the redox agent, targeting compound and chemical drug can be formulated in a single pharmaceutical composition, or each be formulated in a separate pharmaceutical composition.

In a use according to the invention, the targeting compound can be two or more targeting compounds, and the two or more targeting compounds and a chemical drug can be formulated in a single pharmaceutical composition, or each be formulated in a separate pharmaceutical composition.

In a use according to the invention, the chemical drug can be two or more chemical drugs, and the two or more chemical drugs and a targeting compound can be formulated in a single pharmaceutical composition, or each be formulated in a separate pharmaceutical composition.

In a use according to the invention, one of said two or more chemical drugs could be a hapten.

In a use according to the invention, the hapten is nitroimidazole, trinitrophenol (TNP), dinitrophenol (DNP), N-iodoacetyl-N'-(5-sulfonic 1-naphtyl)ethylene diamine (AED), dinitrofluorobenzene (DNFB).

In a use according to the invention, the combination further comprises an anti-neoplasm agent.

In a use according to the invention, the anti-neoplasm agent is an antiangiogenic agent.

In a use according to the invention, the anti-neoplasm agent is selected from the group consisting of an alkylating agent, an antimetabolite, a natural product, a platinum coordination complex, an anthracenedione, a substituted urea, a methylhydrazine derivative, an adrenocortical suppressant, a hormone, and an antagonist.

In a use according to the invention, the anti-neoplasm agent is an oncogene inhibitor or a tumor suppressor gene or protein.

In a use according to the invention, the oncogene inhibitor is an antioncogene antibody or an anti-oncogene antisense oligonucleotide.

In a use according to the invention, the neoplasm to be treated is selected from the group consisting of adrenal gland, anus, auditory nerve, bile ducts, bladder, bone, osseous metastastic, brain, breast, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve and vulva neoplasms, lymph and lymph node metastases of various cancers, and malignant lymphoma.

In a use according to the invention, the neoplasm to be treated is, but is not limited to, a solid tumor.

In a use according to the invention, the size of the solid tumor is larger than $10^8$ cells.

In a use according to the invention, the size of the solid tumor is from about $5\times10^9$ to about $10^{11}$ cells.

In a use according to the invention, the agents are administered to the neoplasm via intravenous injection or direct injection.

In a use according to the invention, the agents are administered to the neoplasm in combination with a surgical procedure.

Particular compositions and combinations are described in the sections and subsections as follows.

MODES FOR CARRYING OUT THE INVENTION

Provided herein are combinations and compositions and methods for systemic tumor combination chemotherapy induced immunotherapy involving neoplasm, tumor and cancer tissues, and preferably combined with intratumoral, gene therapy, and radiotherapy. It is disclosed herein that the systemic immunotherapy induced at the same time as the neoplasm, tumor and cancer tissues are killed by chemotherapy and as the in situ delivery of a hapten to tumor, is a characteristic and effective treatment for such neoplasm, tumor or cancer.

Although not wished to be bound by any theories or mechanisms described herein, it is the current understanding that the following targeting chemotherapy is an effective treatment for neoplasm and can induce some immunotherapic effects simultaneously using a target compound to deliver the hapten and the chemotherapeutic agent to the tissue site simultaneously, which greatly enhances the chemotherapy induced immunotherapy and has a more active contribute to the treatment of neoplasms, tumors and cancers. First, the treatment mediated by the chemical carrier means, kills at least some, in many cases more than 50% of the neoplastic cells in a target tumor. In general, the reduction of the neoplasm mass burden reduces the size of the neoplasm, beneficial to the subsequent immunotherapy. In addition, chemotherapy also results in structural changes in the cell surface, the extracellular matrix and cell lysis to release the contents of the neoplastic cells, i.e., local inflammation. This inflammatory effect, coupled with the added hapten, which is combined with the tumor-specific antigen due to neoplastic cell lysis by local chemodrugs, further generates more complex immunogens. This inflammatory area attracts various lymphocytes, such as the tumor antigen presenting cells (APCs), macrophages, dendritic cells (DCs) and activated B cells, to the area and interact with the tumor antigens, e.g., the complex tumor antigens, DNAs, RNAs and other contents released from the cell lysis. These interactions induce a tumor-specific immune response, which includes humoral, cellular and complement-mediated response. This local tumor-specific immune response is further enhanced by the presence of adjacent live neoplastic cells not initially killed by the local chemodrugs. In this way, the subsequent tumor-specific immune response augments the effect of the chemotherapy (in situ vaccination) and extends to the metastasized neoplastic sites preventing recurrence and metastasis of the neoplastic cells.

The present combinations and methods may also exert their therapeutic effects through their effects on extracellular matrix (EM) upon the carrier reach the tissue area including tumor tissue area. In vivo, tumor cells are surrounded by the extracellular matrix such as collagen, fibronectin, proteoglycans (protein/carbohydrate), hyaluronic acid and other high molecular weight substances. It has been shown that there are differences between the EM of tumor and that of normal tissues.

The tumor-specific immune response can be augmented by in situ administering or by including in the combination of a targeting compound, a facilitating agent that facilitates conjugation between the hapten and a tumor antigen, an immune response potentiator, an anti-neoplastic agent, an oncogene product or any combination thereof.

The contemplated treatment can be used alone or can be used in conjunction with other cancer therapies, such as, but are not limited to, surgery, radiation therapy, chemotherapy and traditional immunotherapy. For example, this treatment can be used with chemotherapy by including various anti-neoplastic agents, such as an anti-angiogenic agent, in the targeting composition. This combination treatment is advantageous because the targeted carrier enhances retention of the anti-neoplastic agents within the neoplastic mass, thereby exposing the neoplastic mass to the anti-neoplasm agent for longer time. In this aspect, the targeting compound acts as a controlled drug-release vehicle.

In summary, the targeted chemotherapy eliminates at least some or more than 50% of the neoplastic cells in the target tumor. The neoplastic cells killed by the anti-neoplastic agents or the survived can be further bound by the hapten modified lysis of tumor cells killed by chemodrug, resulting in the effect of immunotherapy. The in situ "vaccination" further eliminates living neoplastic cells, resulting in better therapeutic efficacy than any of the separate treatments.

In one example, the treatment can be used with radiation therapy by including a radiation sensitizer in the targeting composition. In this aspect, the targeting compound acts as controlled drug release vehicle to release the radiation sensitizer to the living neoplastic cells and increases radiation therapy efficacy.

In another example, the treatment can be used before surgery. In this aspect, the targeting compound composition plays an important role for the pretreatment of neoplasm and makes it easier for surgeon to remove the neoplastic mass and reduces the neoplasm metastasis rate.

In still another example, the treatment can be used with gene therapy by including nucleic acid encoding a desired wild-type oncogene, tumor suppressor gene, immune cytokine gene or apoptosis gene in the targeted carrier composition. This combination treatment is advantageous because the targeting compound may facilitate the delivery of these wild-type oncogenes or tumor suppressor genes into live neoplastic cells.

In all treatments, an immunological adjuvant, such as BCG, can be used in combination with the targeted carrier composition to augment the immune response to the tumor cells. The immunological adjuvants can be injected repeatedly, e.g., every 2 to 4 weeks. Low-dose, e.g., 200 to 300 mg/m$^2$ cyclophosphamide can also be administered prior to, e.g., 3 days, each in situ vaccination to augment the development of cell-mediated immunity to the antigens.

DEFINITIONS

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety. If a definition set forth in this section is contrary to or otherwise inconsistent with a definition set forth in patents, applications, published applications and other publications and sequences from GenBank and other databases that are herein incorporated by reference, the definition set forth in this section prevails over the definition that is incorporated herein by reference.

As used herein, a "conjugate" refers to substances linked together by various interactions, including various compositions, compounds, chelates, linkers, e.g., but not limited to, a conjugate between a targeted compound and an adjuvant. A conjugate comprising a targeting compound is a substance formed by linking a targeting compound and other substance together, which, upon targeted to the target, delivers the substance linked thereto to the target.

As used herein, "a" or "an" means "at least one" or "one or more".

As used herein, an oxidation-reduction reaction refers to a reaction in which electrons are transferred from a donor to an acceptor molecule.

As used herein, an oxidizing agent (or oxidant) refers to an agent that accepts electrons in an oxidation-reduction reaction.

As used herein, a reducing agent (or reductant) refers to an agent that donates electrons in an oxidation-reduction reaction.

As used herein, a targeted carrier refers to a compound that is capable of delivering a compound in a targeted manner. In other words, it means a compound or a bio-substance, which is capable of reaching the specific tissue partly or completely.

As used herein, hapten refers to an antibody-specific substance that cannot induce antibody formation unless bound to a carrier or molecules. Once a hapten is conjugated to a carrier/molecule, the antibody produced using the conjugate may recognize the hapten and/or the carrier/portion. The conjugate of hapten-carrier/molecule may also generate specific cellular immune response.

As used herein, an anti-neoplastic treatment refers to any treatment designed to treat the neoplasm, tumor or cancer by lessening or ameliorating its symptoms. Treatments that prevent the occurrence of neoplasm, tumor or cancer or lessen its severity are also contemplated.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, malignant, as applies to tumors, refers to primary tumors that have the capacity of metastasis with loss of both growth control and positional control.

As used herein, an anti-neoplasm agent (used interchangeably with anti-neoplastic agent, anti-tumor or anti-cancer agent) refers to any agents used in the anti-neoplasm treatment. These include any agents, that when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein. Anti-neoplastic agents include, but are not limited to, anti-angiogenic agents, alkylating agents, antimetabolites, certain natural products, platinum coordination complexes, anthracenediones, substituted ureas, methylhydrazine derivatives, adrenocortical suppressants, certain hormones and antagonists, anticancer polysaccharides and certain herb extracts such as Chinese herb extracts.

As used herein, anti-neoplasm agent (or anti-tumor or anti-cancer agent) or anti-neoplasm treatment does not encompass a combination comprising an oxidizing agent or a reducing agent, and a hapten, or use thereof for treatment, but encompasses all agents and treatment modalities known to those of skill in the art to ameliorate the symptoms in some manner of a neoplasm, tumor or cancer.

As used herein, "angiogenesis" refers to the generation of new blood vessels from parent microvessels. Angiogenesis is highly regulated by a system of angiogenic stimulators and inhibitors. Pathological angiogenesis is caused by a shift in the net balance between stimulators and inhibitors of angiogenesis, e.g., due to the overproduction of normal or aberrant forms of angiogenic mediators, or due to a relative deficiency in inhibitors of this process.

As used herein, "undesired and/or uncontrolled angiogenesis" refers to pathological angiogenesis wherein the influence of angiogenesis stimulators outweighs the influence of angiogenesis inhibitors.

As used herein, "anti-angiogenic treatment or agent" refers to any therapeutic regimen and compound, when used alone or in combination with other treatments or compounds, that can alleviate, reduce, ameliorate, prevent, or place or maintain in a state of remission of clinical symptoms or diagnostic markers associated with undesired and/or uncontrolled angiogenesis. As used herein, "inhibitor of an endotheliase" is not considered an "anti-angiogenic treatment or agent".

As used herein, "tumor suppressor gene" (or anti-oncogene, cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wilm's tumor), DCC (delete in colon carcinoma), NF-1 (neurofibrosarcoma) and APC (adenomatous polypospis coli).

As used herein, "oncogene" refers to a mutated and/or overexpressed version of a normal gene of animal cells (the proto-oncogene) that in a dominant fashion can release the cell from normal restraints on growth, and thus alone, or in concert with other changes, convert a cell into a tumor cell. Exemplary oncogenes include, but are not limited to, abl, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk, and yes.

As used herein, "antisense oligonucleotides" refer to synthetic sequences of nucleotide bases complementary to mRNA or the sense strand of double stranded DNA. Admixture of sense and antisense oligonucleotides under appropriate conditions leads to the binding of the two molecules, or hybridization. When these oligonucleotides bind to (hybridize with) mRNA, inhibition of protein synthesis (translation) occurs. When these oligonucleotides bind to double strand DNA, inhibition of RNA synthesis (transcription) occurs. The resulting inhibition of translation and/or transcription leads to an inhibition of the synthesis of the protein encoded by the sense strand.

As used herein, antibody includes antibody fragments, such as Fab fragments, which are composed of the variable region of a heavy chain and a light chain.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "a facilitating agent that facilitates conjugation between the hapten and a tumor antigen" refers to an agent that links the hapten to the tumor antigen, or any agent that facilitates such linkage. The linkage between the hapten and the tumor antigen can be covalent or non-covalent, and can be mediated by hydrophobic, polar, ionic, electrostatic or other interactions.

As used herein, "immune response" refers to alteration in the reactivity of an organism's immune system in response to an antigen; in vertebrates, this may involve antibody production, induction of cell-mediated immunity, complement activation or development of immunological tolerance.

As used herein, "immune response potentiator" refers to a substance that enhances an antigen's effect in eliciting an immune response.

As used herein, a cytokine is a factor, such as lymphokine or monokine, which is produced by cells that affect the same or other cells. A "cytokine" is one of the groups of molecules involved in signaling between cells during immune responses. Cytokines are proteins or peptides; and some are glycoproteins.

As used herein, "interleukin (IL)" refers to a large group of cytokines produced mainly by T cells, although some are also produced by mononuclear phagocytes, or by tissue cells. They have a variety of functions, but most of them are involved in directing other cells to divide and differentiate. Each interleukin acts on specific, limited group of cells, which express the correct receptors for that cytokine.

As used herein, "interleukin-1 (IL-1)" refers to interleukins made by certain antigen presenting cells (APCs) that, along with IL-6, act as co-stimulatory signals for T cell activation. The IL-1 gene family includes IL-1α, IL-1β, and IL-1 receptor antagonist (IL-1Rα) (Dinarello, Eur. Cytokine Netw. 5(6): 517-522 (1994)). Each member is first synthesized as a precursor protein; the precursors for IL-1 (proIL-1α and proIL-1β) have molecular weights of about 31,000 Da. ProIL-1α and mature 17,000 Da IL-1α are both biologically active whereas the ProIL-1β requires cleavage to a 17,000 Da peptide for optimal biological activity. The IL-1Rα precursor has a leader sequence and is cleaved to its mature form and secreted like most proteins. IL-1α and IL-1β are potent agonists where IL-1Rα is a specific receptor antagonist. Moreover, IL-1Rα appears to be a pure receptor antagonist with no agonist activity in vitro or in vivo. Although IL-1Rα is a secreted protein, there is another form of this molecule that is retained inside cells. It is called "intracellular" (ic) IL-1Rα. IcIL-1Rα results from alternate mRNA splice insertion of the IL-1Rα gene replacing the exon coding for the signal peptide. The IL-1Rα forms are functionally indistinguishable.

Thus, reference, for example, to "IL-1" encompasses all proteins encoded by the IL-1 gene family including IL-1α, IL-1β, IL-1Rα and icIL-1Rα, or an equivalent molecule obtained from any other source or that has been prepared synthetically. It is intended to encompass IL-1 with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al., Molecular Biology of the Gene, 4th Edition, 1987, The Bejacmin/Cummings Pub. co., p. 224).

Such substitutions are preferably made in accordance with those set forth in Table 2 as follows:

TABLE 2

| Original residue | Conservative substitution |
| --- | --- |
| Ala (A) | Gly; Ser |
| Arg (R) | Lys |
| Asn | (N) |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |

TABLE 2-continued

| Original residue | Conservative substitution |
| --- | --- |
| Tyr (Y) | Trp; Phe |
| Val (V) | Ile; Leu |

Other substitutions are also permissible and may be determined empirically or in accord with known conservative substitutions.

As used herein, the amino acids, which occur in the various amino acid sequences appearing herein, are identified according to their well-known three-letter or one-letter abbreviations. The nucleotides, which occur in the various DNA fragments, are designated with the standard single-letter designations used routinely in the art.

As used herein, the terms "a therapeutic agent", "therapeutic regimen", "radioprotectant", "chemotherapeutic" mean conventional drugs and drug therapies, including vaccines, which are known to those skilled in the art. "Radiotherapeutic" agents are well known in the art.

As used herein, "vaccine" refers to any compositions intended for active immunological prophylaxis. A vaccine may be used therapeutically to treat a disease, or to prevent development of a disease or to decrease the severity of a disease either proactively or after infection. Exemplary vaccines include, but are not limited to, preparations of killed microbes of virulent strains or living microbes of attenuated (variant or mutant) strains, or microbial, fungal, plant, protozoa, or metazoa derivatives or products. "Vaccine" also encompasses protein/peptide and nucleotide based vaccines.

As used herein, "cytotoxic cells" refers to cells that kill virally infected target cells expressing antigenic peptides presented by MEW class I molecules.

As used herein, "serum" refers to the fluid portion of the blood obtained after removal of the fibrin clot and blood cells, distinguished from the plasma in circulating blood.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, treatment means any manner in which the symptoms of conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical or chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry, A Biochemical Approach, Oxford University Press, New York, pages 388-392).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities. Thus, for purposes herein the biological activity of a luciferase is its oxygenase activity whereby, upon oxidation of a substrate, light is produced.

As used herein, a receptor refers to a molecule that has an affinity for a given ligand. Receptors may be naturally occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases;

c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of the variable region of a heavy chain and a light chain.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, production by recombinant means by using recombinant DNA methods means the use of the well-known methods of molecular biology for expressing proteins encoded by cloned DNA.

As used herein, substantially identical to a product means sufficiently similar so that the property of interest is sufficiently unchanged so that the substantially identical product can be used in place of the product.

As used herein, equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions [see, e.g., Table 2, above] that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary", when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein, stringency of hybridization in determining percentage mismatch is as follows:

1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, a composition refers to any mixture. It may be a solution, a suspension, liquid, powder, a paste, aqueous, non-aqueous or any combination thereof.

As used herein, a combination refers to any association between two or among more items. Combinations include compositions in which two or more components are contained in a single mixture; it also includes two separate combinations that are associated.

As used herein, fluid refers to any composition that can flow. Fluids thus encompass compositions that are in the form of semi-solids, pastes, solutions, aqueous mixtures, gels, lotions, creams and other such compositions.

As used herein, the abbreviations for any protective groups, amino acids and other compounds, are, unless indicated otherwise, in accord with their common usage, recognized abbreviations, or the International Union of Pure and Applied Chemistry—International Union of Biochemistry (IUPAC-IUB) Commission on Biochemical Nomenclature (see, (1972) Biochem. 11: 1726).

For clarity of disclosure, and not by way of limitation, the detailed description of the invention is divided into the subsections that follow.

Combinations

In a specific embodiment, provided herein is a combination useful for tumor therapy, which combination comprises: a) an oxidizing agent and/or a reducing agent; b) a targeting carrier and anti-cancer drug; and c) a hapten.

The oxidizing or reducing agent, the targeting carrier and anti-cancer drug and the hapten cannot be formulated in a single pharmaceutical composition but each can be formulated in a separate pharmaceutical composition. Before using, each of component were mixed to be conjugated by chemical non-covalent reaction.

Any oxidizing agent that is bio-tolerable can be used in the combination. In a preferred embodiment, the oxidizing agent used is selected from the group consisting of stannous chloride (SnCl2), stannous sulfate (SnSO3), stannous oxide (SnO), stannic oxide (SnO2), sodium stannate (Na2SnO3), sodium stannite (Na2SnO2), stannous chloride (SnCl2), stannic chloride (SnCl4), thiostannate (SnS3), and stannous sulfide (SnS).

Any reducing agent that is bio-tolerable can be used in the combination. In a preferred embodiment, the reducing agent used is hematoxylin, a hypoxic reducing agent such as a nitroimidazole, or nonnitro compound tirapazamine (SR-4233) (Zhang and Stevens, Melanoma Res., 8 (6): 510-5 (1998)).

Any targeting compound can be used in the combination. In a preferred embodiment, the targeting compound used in selected from the group consisting of, but not limited to: Sodium Dimercaptosuccinate (DMSA-III), Sodium Dimercaptosuccinate (DMSA-V), Sodium Pyrophosphate and Stannous Chloride for Injection (PYP), Methylene diphosphonate Injection (MDP); polyalbumin; mercaptoacetyltriglycine; Pentetic Acid and Stannous Chloride (DTPA), Sodium Glucoheptonate and Stannous Chloride; L,L-Ethyl Cysteinate Dimer and Stannous Chloride (ECD), Exametazime (HMPAO), Etifenin and Stannous Chloride, Sodium Phytate and Stahnous Chloride, [Cu(MIBI)4BF4](MIBI); a-methyltyosine; MIBI (2-methoxy isobutyl isonitrile); 2-nitroimidazole; monoclonal antibodies and monoclonal antibodies against tumor, and traditional Chinese medicine extracts, such as Bruceantin, Tetrandrine, thalicarpine, maytansine like as Table 1.

Any hapten that is bio-tolerable can be used in the combination. In a preferred embodiment, the hapten used is trinitrophenol (TNP) (Dieli et al., Int. Immunol. 9 (1): 1-8 (1997)), dinitrophenol (DNP) (Stjamkvist et al., J. Pharm. Sci., 80 (5): 436-40 (1991)), N-iodoacetyl-N'-(5-sulfonic 1-naphtyl)ethylene diamine (AED) (Mizuochi et al., J. Immunol. 134 (2): 673-6 (1985)), dinitrofluorobenzene (DNFB) (Claman, J: Immunol. 116(3): 704-9 (1976)) or Ovabulin (OVA) (Katz et al., J: Immunol. 107 (5): 1319-28(1971))

In another specific embodiment, the combination further comprises an anti-neoplasm agent for combined intravenous therapy and chemotherapy.

Any anti-neoplasm agents can be used in the combination. In a preferred embodiment, the anti-neoplasm agent used is an anti-angiogenic agent. More preferably, the anti-angiogenic agent is an inhibitor of basement membrane degradation, an inhibitor of cell migration, an inhibitor of endothelial cell proliferation, and an inhibitor of three-dimensional organization and establishment of potency. Examples of such anti-angiogenic agent are further illustrated in the following Table 3 (Auerbach and Auerbach, Pharmacol. Ther. 63(3): 265-311 (1994)).

TABLE 3

| Anti-angiogenic agents | | |
|---|---|---|
| Type | Subtypes | Examples |
| Inhibitors of basement membrane degradation | Inhibitors of Protease inhibitors | Plasminogen activators (e.g. PAI-1, PAI-2) tissue inhibitors of metalloproteinases (e.g., TIMP-1 and TIMP-2) phenylalanyl-propyl-arginine chloromethyl ketone-thrombin |
| | Cartilage-derived inhibitors | Cartilage-derived inhibitor (CDI) |
| | Epithelium-derived inhibitors | |
| | Phorbol esters | 1-10-phenanthroline |
| | Steriods | Medroxyprogesterone acetate, dexamethasone, medroxyprogeste-rone, triamcinolone acetonide, proline analogs and trans-retinoic acid, analogues of somatostatin |
| | Antibiotics | minocycline, sulphonated derivatives of distamycin A |

TABLE 3-continued

Anti-angiogenic agents

| Type | Subtypes | Examples |
| --- | --- | --- |
| Inhibitors of cell migration | Taxol, colchicine, vinblastine, nocodazole | Taxol, colchicine, vinblastine, nocodazole |
| | Interferons | Leukocyte (α/β) IFN |
| | Cholera toxin | |
| | TGFβ family | |
| | α-Difluoromethyl ornithine and other inhibitors of ornithine decarboxylase | |
| | Inhibitors of FGF: protanine, PF4, suramin | |
| | Corticosteroids and heparin | Hexosaminoglycan sulfate |
| | Interleukin-8 | |
| | SPARC | SPARC ("Secreted Protein, Acidic and Rich in Cysteines") |
| | Inhibitors of platelet-activating factor | *Bothrops jararaca* venon |
| | Targeting mast cells and macrophages: thiols and gold-containing compounds | |
| | Targeting lymphocytes: steroids, anti-lymphocyte sera, irradiation | Cyclosporin opioids such as β-endorphin or morphine sulfate, AGM-1470 |
| | Targeting the extracellular matrix: peptides, antibodies, sulfated chitin derivatives | |
| | Heparin | |
| | Prostaglandins inhibitors | prostaglandin synthesis, like indomethacin and aspirin, ketorolac, mitoxantrone or bisantrene, α-guiaconic acid and their derivatives, amiloride |
| | Placental ribonuclease inhibitor | RNasin, glycine-arginine-glycine-inhibitor asparagine-serine (GRGDS), actin and an anti-actin antibody inhibitor |
| | Antibiotics | herbamycin, bleomycin, eponemycin, erbstatin, radicicol and staurosporine |
| | Other inhibitors of cell migration | Nicardipine, sphingosine-1-phosphate, linomide (N-phenylmethyl-1, 2-dihydro-4-hydroxyl-1-methyl-2-oxoquinoline-3-carboxamide), platelet-endothelial cell adhesion molecule-1 (PECAM-1) |
| Inhibitors of endothelial cell proliferation | Inhibitors of fibroblast growth factor | Blocking antibodies to FGF, pentosan, polysulfate, heparinase, protamine, somatostatin analogues, such as octreotide |
| | Thrombospondins | TSP1, TSP2 and TSP3 |
| | Phorbol esters | |
| | Retinoids | Etretin, etretinate or isotretinoin, acitretin, genistein |
| | The TGFβs | TGFβ, TGFβ1 and TGFβ2 |
| | Tumor necrosis factor, interfereons, interleukins and other cytokines | TNF, IL-1, IFN-A, IFN-a and macrophage-derived endothelial cell inhibitor |
| | Steroids and heparin | Tetrahydro S, hydrocortisone, β-cyclodextrin tetradecasulfate, estrogen metabolites such as 2-methoxyoestradiol, steriods were coadministered with DS4152, a bacterially derived sulfated polysaccharide complex |
| | Suramin | Suramin, a polysulfonated urea |
| | α2-Macroglobulin | |
| | Antibodies to growth factors | Antibodies to bFGF, antibodies to peptides of VEGF, hepatocyte growth factor (scatter factor), anti-scatter factor antibodies |
| | Anti-angiogenic peptides | The 16 kDa fragment of prolactin, heparin-binding peptide-fragments from fibronectin, selected peptides of TSP, atrial natriuretic polypeptide, PF4, a non-heparin-binding analog of PF4, rPF4-241 |
| | Retina-derived inhibitors | Crude extract of the retina in combination with adult serum |

TABLE 3-continued

Anti-angiogenic agents

| Type | Subtypes | Examples |
|---|---|---|
| | Antibiotics | Rapamycin, eponemycin, the spermidine moiety-containing compound 15-deoxyspergualin, TAN-1120, a baumycin-group anthracycline, d-penicillamine, fumagillin, as well as its more potent synthetic analogue AGM-1470 (TNP-470), FR-111142, which was isolated from strain F-2015 of *Scolecobasiwn arenarium*, WF-16775A$_1$ and A$_2$, isolated from *Chaetasbolisia erysiphoides*, SP-PG (or its most active component, DS-4152), a sulfated polysaccharide-peptidoglycan complex produced by an *Arthobacter* species, tetracyclines, minocycline |
| | Glycosaminoglycans SPARC SPARC | Hyaluronan |
| | Other pharmacological agents | Chloroquine, magnosalin, sulfapyridine, agents several opioids, gold compounds, dimethyl sulfoxide |
| Inhibitors of three-dimensional organization and establishment of potency of new blood vessels | The TGFβs | TGFβ1, TGFβ2, TGFβ3 |
| | Interferons | IFN-γ, IFN-α |
| | Fatty acids | |
| | Oxazolones | MD 27032 (4-propyl-5 (4-pyridinyl-2 (3H)-oxazolone) |
| | Inhibitors of basement membrane biosynthesis | Cyclic adenosine monophosphate, cis-hydroxy-proline, an inhibitor of collagen production |
| | Inhibitors of cell adhesion molecules | YSIGR-containing peptides, Arg-Gly-Asp molecules (RGD)-containing peptide Gly-Arg-Gly-Asp-Ser (GRGDS), vitronectin, fibronectin, antibodies, αvβ3 integrins, antibodies to αvβ3 integrins, antibodies to E-selectin, sialyl Lewis-X ligand |
| | Other inhibitors of three-dimensional organization of endothelial cells | Nicardipine, phosphokinase C inhibitors, such as calphostin C and staurosporine, a chimeric toxin in which aFGF was fused to mutant forms of *Pseudomonas* exotoxin, IL-1β, IL-6, TGF-β and platelet-derived growth factor-BB, irsogladine, fenretinide, a proline analog, L-adetine-2-carboxylic acid, cyclosporine, the 16 kDa fragment of prolactin |
| Physiological and physical interventions | Cell-cell interactions | pericyte, endothelial-pericyte interactions, physical interventions cocultures of cardiac microvascular endothelial cells and ventricular myocytes |
| | Blood flow | |
| | Photodynamic therapy | Photocoagulation of photodynamic therapy |
| | Hyperthermia | The effect of hyperthermia may be exerted by a combination of endothelial cell killing, inhibition of replication, inhibition of cell migration or by a combination of these mechanisms |
| | Hypoxia | |

In another preferred embodiment, the anti-angiogenic agent used is AGM-1470 (TNP-470), angiostatic steroids, angiostatin, antibodies against αvβ3, antibodies against bFGF, antibodies against IL-1, antibodies against TNF-α, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, gelatinase inhibitor, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, matrix metalloproteinase inhibitor, marimastat (BB-2516), medroxyprogesterone, 6-methylmercaptopurine riboside, metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4 (PF4), prednisolone, prolactin (16-Kda fragment), proliferin-related protein, prostaglandin synthase inhibitor, protamine, retinoids, Roquinimex (LS-2616. linomide), somatostatin, stromelysin inhibitor, substance P, suramin, SU101, tecogalan sodium (DS-4152), tetrahydrocortisol-sthrombospondins (TSPs), tissue inhibitor of metalloproteinases (TIMP 1, 2,3), vascular endothelial growth factor inhibitors, vitamin A, Vitaxin, vitreous fluids, thalidomide, 3-aminothalidomide, 3-hydroxythalidomide and metabolites or hydrolysis products of thalidomide, 3-aminothalidomide, or 3-hydroxythalidomide (((O'Reilly, Investigational New Drugs, 15: 5-13 (1997); J. Nat'l Cancer Instit., 88 786-788 (1996); U.S. Pat. Nos. 5,593,990, 5,629,327 and 5,712,291). Also preferably, the anti-angiogenic agent used is an angiostatic gene such as angiostain, endostain, kringle-5, PEX, TIMP-1, TIMP-2, TIMP-3, TIMP-4, endo: angio, or endo: PEX; or an angiostatic chemokine genes such as IP-10, Mig, or SDF-1α.

In still another preferred embodiment, the anti-neoplasm agent used is an alkylating agent, an antimetabolite, a natural product, a platinum coordination complex, an anthracenedione, a substituted urea, a methylhydrazine derivative, an adrenocortical suppressant, a hormone and an antagonist. Examples of such anti-neoplasm agents are further illustrated in the following Table 4:

TABLE 4

Chemotherapeutic Agents Useful in Neoplastic Disease

| CLASS | TYPE OF AGENT | NONPROPRIETARY NAMES | DISEASE |
| --- | --- | --- | --- |
| Alkylating Agents | Nitrogen Mustards | Mechlorethamine | Hodgkin's disease, non-Agents Hodgkin's lymphomas |
| | | Cyclophosphamide | Acute and chronic lymphocytic leukemias, Hodgkin's disease, non-Hodgkin's lymphomas, multiple myeloma, neuroblastoma, breast, ovary, lung, Wilms'tumor, cervix, testes, soft-tissue sarcomas |
| | | Melphalan (L-sarcolysin) | Multiple myeloma, breast, ovary sarcoma |
| | | Chlorambucil | Chronic lymphocytic leukemia, primary macroglobulinemia, Hodgkin's disease, non-Hodgkin's lymphomas |
| | Ethylenimines and Methylmelanines | Hexamethyhnelanine | Ovary |
| | | Thiotepa | Bladder, breast, ovary |
| | Alkly Sulfonates | Busulfan | Chronic Granulocytic leukemia |
| | Nitrosourea | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazenes | Dacarbazine (DTIC; dimethyltriazenoimidazole-carboxamide) | Malignant melanoma, Hodgkin's disease, soft-tissue sarcomas |
| Antimetabolites | Folic Acid Analogs | Methotrexate (amethopterin) | Acute lymphocytic choriocarcinoma, mycosis fungoides, breast, head and neck, lung, osteogenic sarcoma |
| | Pyrimidine Analogs | Fluorouacil (5-fluorouracil; 5-FU) Floxuridine (fluorodeoxyuridine; FUdR) | Breast, colon, stomach, pancreas, ovary, head and neck, urinary bladder, pre-malignant skin lesions (topical) |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic, and chronic granulocytic leukemias |
| | | Thioguanine (6-thioguanine; TG) | Acute granulocytic, acute lymphocytic, and chronic granulocytic leukemias |
| | | Pentostatin (2'-deoxycoformycin) | Hairy cell leukemia, mycosis fungoides, chronic lymphocytic leukemia |

TABLE 4-continued

Chemotherapeutic Agents Useful in Neoplastic Disease

| CLASS | TYPE OF AGENT | NONPROPRIETARY NAMES | DISEASE |
|---|---|---|---|
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wihns'tumor, rhabdomyosarcoma, Hodgkin's disease, non-Hodgkin's lymphomas, small-cell lung |
| | Epipodophyllotoxins | Etoposide, Teniposide | Testis, small-cell lung and other lung, breast, Hodgkin's disease, non-Hodgkin's lymphomas acute granulocytic leukemia, Kaposi's sarcoma |
| | Antibiotics | Dactinomycin (actinomycin D) | Choriocarcinoma, Wilms' tumor, rhab-domyosarcoma, testis, Kaposi sarcoma |
| | | Daunorubicin (daunomycin; rubidomycin) | Acute granulocytic and acute lymphocytic leukemias |
| | | Doxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas, |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon-alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methylhydrazine Derivative | Procarbazine (N-methylhydrazine MIH) | Hodgkin's disease |
| | Adrenocortical Suppressant | Mitotane (o, p'-DDD) | Adrenal cortex |
| Hormone and Antagonists | Adrenocortico-steriods | Prednisone (several other equivalent preparations lymphocytic leukemias, available; see Chapter 59) | Acute and chronic non-Hodgkin's lymphomas, Hodgkin's disease, breast |
| | Progestins | Hydroxyprogesterone caproate Medroxyprogesterone acetate Megestrol acetate | Endometrium, breast |

TABLE 4-continued

Chemotherapeutic Agents Useful in Neoplastic Disease

| CLASS | TYPE OF AGENT | NONPROPRIETARY NAMES | DISEASE |
|---|---|---|---|
| | Estrogens | Diethylstilbestrol Ethinyl estradiol (other preparations available; see Chapter 57) | Breast prostate |
| | Antiestrogen | Tamoxifen | Breast |
| | Androgens | Testosterone propionate Fluoxymesterone (other preparations available; see Chapter 58) | Breast |
| | Antiandrogen | Flutamide | Prostate |
| | Gonadotropin-Releasing Hormone Analog | Leuprolide | Prostate |

In yet another preferred embodiment, the anti-neoplasm agent used is cytosine analogues such as Cytidine Arabinosyladenine (Ara-C), Daunomycin, Doxorubicin, Methotrexate (MTX); Fluorinated pyrimidines such as 5-Fluorouracil (5-FU); Hydroxyurea; 6-mercaptopurine; plant alkaloids such as vincristine (VCR), VP-16 and vinblastine (VLB); alkylating agent such as Cyclophosphamide tumor cell lyses agent, Mesna, Melphalan, BCNU, Cisplatin, Nitrogen Mustard (HN2), Trisamine (HN3); Nonclassic alkylating agent such as Procarbazine; Bleomycin; Mitomycin C; Actinomycin D (DACT); or an enzyme such as L-Asparaginase.

In yet another preferred embodiment, the anti-neoplasm agent used is an oncogene inhibitor. More preferably, the oncogene inhibitor is an anti-oncogene antibody or an anti-oncogene antisense oligonucleotide. For example, antibodies and antisense oligonucleotides against the oncogenes can be used in the combination.

In another embodiment, the anti-neoplastic agent used is a cellular matrix inhibitor. More preferably, the cellular matrix inhibitor is an anti-cellular-matrix antibody or an anti-cellular-matrix antisense oligonucleotide. For example, antibodies and antisense oligonucleotides against the following cellular matrix or cellular matrix gene can be used: caveolin-1, decorin, cadherins, catenins, and integrins.

In another specific embodiment, the combination further comprises a radiation sensitizer for combined intratumoral therapy and radiation therapy. In a preferred embodiment, the radiation sensitizer used is SR 2508 (etanidazole) (Chang et al., Int. J. Radiat. Oncol. Biol. Phys., 40 (1): 65-70 (1998)) or Buthionine sulfoximine (BSO) (Vahrmeijer et al., Cancer Chemother. Pharmacol. 44 (2): 111-6 (1999)).

In another specific embodiment, the combination further comprises a facilitating agent that facilitates conjugation between the hapten and a tumor antigen to enhance the autologous tumor-specific immune response, Preferably, the facilitating agent used is a chelator or a chemical crosslinking agent. More preferably, the chelator used is glycyltyrosyl-(N-e-diethylenetri-aminepetaacetic acid)-lysine (GYK-DTPA) or doxorubicin adipic-dihydrazide (ADR-ADH). Also more preferably, the chemical crosslinking agent used is carbodimide.

In another specific embodiment, the composition further comprises an immune response potentiator to enhance the autologous tumor-specific immune response. Preferably, the potentiator used is Bacille Calmette-Guerin (BCG) (Ratliff, Eur. Urol., 2: 17-21 (1992)), *Corynebacterium Parvum* (Lillehoj et al., Avian Dis., 37 (3: 371-40 (1993)), *Brucella abortus* extract, glucan, levamisole, tilorone, an enzyme, a non-virulent virus, polysaccharides, or herb extracts such as Chinese herb extracts. More preferably, the enzyme used is *Vibrio cholera* neuraminidase (VCN) (Seiler and Sedlacek, Recent Results Cancer Res., 75:53-60 (1980)), Papain (Helting and Nau, Acta Patrol. Microbiol. Immunol. Scand., 92 (1): 59-63 (1984); and Hess, Eur. J Immunol. 6 (3): 188-93 (1976)), β-galactosidase or concanavalin A. Also more preferably, the non-virulent virus used is a non-virulent Newcastle virus (Meulemans et al., Vet. Rec., 143 (11): 300-3 (1998); and Adams, Poult. Sci., 49 (1): 229-33 (1970)). Further more preferably, the polysaccharides used are anti-tumor polysaccharide from the mycelium of liquid-cultured Agarics *blazei mill* (preliminarily glucomannan with a main chain of β-1, 2-linked D-mannopyranosyl residues and β-D-glucopyranosyl-3-O-β-D-glucopyranosyl residues as a side chain (Mizuno et al., Biochem. Mol. Biol. Int., 47(4): 707-14 (1999)); anti-tumor polysaccharide preparation from Flammulina velutipes (The backbones of the polysaccharide is mainly composed of β-(1→3)-D-linked glucose and its molecular weight was estimated to be about 200 KD) (Leung et al., Immunopharmacology, 35(3): 255-63 (1997)); sizofiran (SPG) (Tanji et al., Yakugaku Zasshi, 110(11): 869-75 (1990)); schizophyllan (Sakagami et al., Biochem. Biophys. Res. Commun. 155 (2): 650-5 (1988)); mannan (Gavrilenko et al., Vopr. Onkol. 29(4): 67-70(1983)); lentinan (Haba et al., Int. J Cancer, 18(1): 93-104 (1976)); Su-polysaccharide (Su-Ps) (Kumazawa et al., Gan To Kagaku Ryoho, 14(12): 3329-35(1987)); or mannozym (Zastrow, Padiatr. Grenzgeb. 24 (3): 229-36 (1985)).

In another specific embodiment, the composition can also include a cytokine to enhance the autologous tumor-specific immune response. Preferably, the cytokine is administered as a liposome-encapsulated IL-2 for deposit formulation (Krup et al., J Immunother. 22 (6): 525-38 (1999)), or a GM-CSF storage formulation (the storage formulation is for granulocyte-macrophage colony stimulating factor (GM-CSF)) (Leong et al., J. Immunother. 22 (2): 166-74 (1999)).

In another embodiment, the composition can include a reporter to monitor the treatment progress. The reporter can be a chemical or an enzyme. Preferably, the reporter enzyme is β-galactosidase or its gene. Other reporters known in the art are also contemplated.

The oxidizing agent or reducing agent is administered in a composition at a concentration from about 0.01% (w/w) to about 35% (w/w), targeting compound and chemical drug are from about 1% (w/w) to about 98% (w/w) and the hapten is from about 1 mg/ml to about 80 mg/ml in the composition.

Also provided herein are kits for use in intravenous therapy, which kit include the composition which includes components containing one or more of A) an oxidizing agent or a reducing agent; B) a targeting carrier agent and an anticancer agent; and C) a hapten. The kit can also include syringes for administering the composition(s) and instructions for administration.

Also provided herein is an article of manufacture for use in intravenous therapy. The article of manufacture includes A) packaging material; B) one or more of an oxidizing agent or a reducing agent, a targeting compound and an anticancer agent, and a hapten; and C) a label indicating that the article is for treating neoplasms by intravenous drops.

Methods of Treatment

Provided herein are methods for treating neoplasm in a mammal by in situ administration to a neoplasm of a mammal an effective amount of targeting agent with a hapten and chemical drug(s) that causes death of the neoplasm, whereby tumor lysis is modified by DNP and stimulate to immunological response, and whereby an autologous immune response is generated against the neoplasm and the neoplasm is treated. In a specific embodiment, the mammal treated is a human.

In another specific embodiment, the hapten used is trinitrobenzene (TNP), dinitrobenzene (DNP), N-iodoacetyl-N'-(5-sulfonic 1-naphtyl)ethylene diamide (AED), dinitrofluorobenzene (DNFB).

In still another specific embodiment, the method further comprises in situ administering a facilitating agent that facilitates conjugation between the hapten and a tumor antigen of the neoplasm to enhance the tumor-specific autologous immune response. Preferably, the facilitating agent used is a chelator or a chemical crosslinking agent. More preferably, the chelator used is glycyltyrosyl-(N-e-diethylenetri-aminepetaacetic acid)-lysine (GYK-DTPA) or doxorubicin adipic-dihydrazide (ADR-ADH). Also more preferably, the chemical crosslinking agent is carbodiimide.

In yet another specific embodiment, the method further comprises in situ administering an immune response potentiator to enhance the tumor-specific autologous immune response. Preferably, the immune response potentiator used is Bacille Calmette-Guerin (BCG) (Ratliff, Eur. Urol., 2:17-21 (1992)), *Corynebacterium Parvum* (Lillehoj et al. Avian Dis., 37(3): 371-40 (1993)), *Brucella abortus* extract, glucan, levamisole, tilorone, an enzyme, a non-virulent virus, polysaccharides, or herb extracts such as Chinese herb extracts.

Any means that can target neoplasm tissue carriers or cells, e.g., chemical or physical means, can be used. In a specific embodiment, chemical drugs accumulation in neoplasm is achieved by in situ administration of a composition comprising: A) an oxidizing agent or a reducing agent; and B) a targeting compound agent and an anticancer agent.

The oxidizing or reducing agent, the targeting compound agent and the anticancer agent, and the hapten can be formulated in a single pharmaceutical composition or each can be formulated in a separate pharmaceutical composition.

In a preferable embodiment, the oxidizing agent used includes, but is not limited to, stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannous chloride ($SnCl_2$), stannic chloride ($SnCl_4$), thiostannate ($SnS_3$), and stannous sulfide (SnS).

In another specific embodiment, the targeting compound used includes, but is not limited to, Sodium Dimercaptosuccinate (DMSA-III); Sodium Dimercaptosuccinate (V) (DMSA-V); Sodium Pyrophosphate and Stannous Chloride for Injection (PYP); Methylenediphosphonate Injection (MDP); Albumin Aggregated; Mercaptoacetyltriglycine; Pentetic Acid and Stannous Chloride (DTPA); Sodium Glucoheptonate and Stannous Chloride; L,L-Ethyl Cysteinate Dimer and Stannous Chloride (ECD); Exametazime (HM-PAO); Etifenin and Stannous Chloride; Sodium Phytate and Stannous Chloride; methoxy isobutyl isonitrile salt [Cu (MIBI)4BF4] (MIBI), α-methyltyosine, MIBI (2-methoxy isobutyl isonitrile), nitroimidazole-based compound (2-nitroimidazole), monoclonal antibodies and monoclonal antibodies against tumor, and traditional Chinese drug extract such as Bruceantin, Tetrandrine, thalicarpine, maytansine and the like table 1.

The presently contemplated tumoral therapy can be used alone or can be used in conjunction with other cancer therapies. In a specific embodiment, the tumoral therapy is used in conjunction with chemotherapy by further administering an anti-neoplasm agent to the neoplasm.

Any anti-neoplasm agents can be used. In a preferred embodiment, the anti-neoplasm agent is an anti-angiogenic agent. More preferably, the anti-angiogenic agent used is an inhibitor of basement membrane degradation, an inhibitor of cell migration, an inhibitor of endothelial cell proliferation, and an inhibitor of three-dimensional organization and establishment of potency. Also more preferably, the anti-angiogenic agent used is AGM-1470 (TNP-470), angiostatic steroids, angiostatin, antibodies against avé3, antibodies against bFGF, antibodies against IL-1, antibodies against TNF-ot, antibodies against VEGF, auranofin, azathioprine, BB-94, BB-2516, basic FGF-soluble receptor, carboxyamido-trizole (CAI), cartilage-derived inhibitor (CDI), chitin, chloroquine, cisplatin, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, gelatinase inhibitor, glioma-derived angiogenesis inhibitory factor (GD-AIF), GM 1474, gold chloride, gold thiomalate, heparinases, hyaluronan (high and low molecular-weight species), hydrocortisone/beta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, matrix metalloproteinase inhibitor, marimastat (BB-2516), medroxyprogesterone, 6-methyhnercaptopurine riboside, metastat (Col-3), methotrexate, minocycline, nitric oxide, octreotide (somatostatin analogue), Paclitaxel, D-penicillamine, pentosan polysulfate, placental proliferin-related protein, placental Rnase inhibitor, plasminogen activator inhibitor (PAIs), platelet factor-4 (PF4), prednisolone, prolactin (16-Kd fragment), proliferin-related protein, prostaglandin synthase inhibitor, protamine, retinoids, Roquinimex (LS-2616. linomide), somatostatin, stromelysin inhibitor, substance P, suramin, SU101, tecogalan sodium (DS-4152), tetrahydrocortisol-sthrombospondins (TSPs), tissue inhibitor of metalloproteinases (TIMP 1, 2, 3), vascular endothelial growth factor inhibitors, vitamin A, Vitaxin, vitreous fluids, thalidomide, 3-aminothalidomide, 3-hydroxythalidomide and metabolites or hydrolysis products of thalidomide, 3-aminothalidomide, or 3-hydroxythalidomide. Other anti-angiogenic agents described in Section B can also be used. Also preferably, the anti-angiogenic agent used is an angiostatic gene such as angiostain, endostain, kringle-5, PEX, TIMP-1, TIMP-2, TIMP-3, TIMP-4, endo::angio, or endo::PEX; or an angiostatic chemokine genes such as IP-10, Mig, or SDF-1a.

In another preferred embodiment, the anti-neoplasm agent used is an alkylating agent; an antimetabolite, a natural product, a platinum coordination complex, an anthracenedione, a substituted urea, a methylhydrazine derivative, an adrenocortical suppressant, a hormone, an antagonist, an anti-cancer polysaccharide, or herb extracts such Chinese herb extracts. Additional anti-neoplasm agents described in Section B can also be used.

In another specific embodiment, the method further comprises in situ administering a radiation sensitizer for combined targeting therapy and radiation therapy. In a preferred embodiment, the radiation sensitizer used is antisense raf oligodeoxyribonucleotide (Gokhale et al., Antisense Nucleic Acid Drug Dev., 9 (2): 191-201 (1999); SR 2508 (etanidazole) (Chang et al., Int. J. Radiat. Oncol. Biol. Phys., 40 1: 65-70 (1998)) or Buthionine sulfoximine (BSO) (Vahrmeijer et al., Cancer Chemother. Pharmacol. 44 (2): 111-6 (1999)).

In yet another specific embodiment, the method further comprises in situ administering a reporter to monitor the treatment progress. The reporter can be a chemical or an enzyme. Preferably, the reporter enzyme is β-galactosidase or its gene. Other reporters known in the art are also contemplated.

In a specific embodiment, both TNP and DNP as the hapten are used in the treatment.

In another specific embodiment, the oxidizing agent or reducing agent used is from about 0.01% (w/w) to about 35% (w/w), the targeting compound used is from about 1% (w/w) to about 99% (w/w) and the hapten used is from about 1 mg/ml to about 80 mg/ml in the treatment.

In a specific embodiment, the autologous immune response generated by the combined action of the hapten and the anti-cancer agent or treatment is a humoral and/or cellular immune response.

Any neoplasm, tumor or cancer can be treated by the presently contemplated methods. For example, the neoplasm of adrenal gland, anus, auditory nerve, bile ducts, bladder, bone, brain, breast, bruccal, central nervous system, cervix, colon, ear, endometrium, esophagus, eye, eyelids, fallopian tube, gastrointestinal tract, head and neck, heart, kidney, larynx, liver, lung, mandible, mandibular condyle, maxilla, mouth, nasopharynx, nose, oral cavity, ovary, pancreas, parotid gland, penis, pinna, pituitary, prostate gland, rectum, retina, salivary glands, skin, small intestine, spinal cord, stomach, testes, thyroid, tonsil, urethra, uterus, vagina, vestibulocochlear nerve or vulva neoplasm, various cancer lymph and lymph node metastatic lesion and malignant lymphoma can be treated.

Other examples of tumors or cancers treatable by the present methods include breast cancer, lung cancer, colonrectal cancer, tumor of the pancreas, gallbladder and extrahepatic ducts, tumor of liver, gastric neoplasms, cancer of the esophagus, malignant melanoma, urologic and male genitals cancers, skin cancer, head neck and thyroid cancer, cancer of the central nervous system and pituitary, tumor of the eye and ocular adnexa, malignant tumor of bone, soft tissue sarcoma, Hodgkin's disease and non-Hodgkin's disease, multiple myeloma, pediatric solid tumor, gynecologic cancer. Additional examples include:

A. Tumor of mesenchymal origin: (1) Connective tissue and derivatives: Sarcomas: fibrosarcoma, myxosarcoma, liposarcoma, chondrosarcoma, osteogenic sarcoma (2) Endothelial and related tissues blood vessels: angiosarcoma, lymphangiosarcoma, synovioma, mesotheliomas, invasive meningioma.

B. Tumor of epithelial origin: (1) Stratified squamous: carcinoma, squamous cell or epidermoid carcinoma (2) Basal cells of skin or adnexa: basal cell carcinoma (3) Skin adnexalglands: Sweat gland carcinoma, sebaceous gland carcinoma (4) Epithelial lining: Adenocarcinoma, papillary carcinoma, papillary adenocarcinoma, cystadenocarcinoma, medullary carcinoma, undifferentiated carcinoma (5) Respiratory passage: Bronchogenic adenoma (6) Neuroectoderm: Melanoma, (7) Renal epithelium: Renal cell carcinoma, hypernephroma (8) Liver cells: Hepatoma (hepatocellular carcinoma) (9) Bile duct: Bile duct carcinoma, chlangiocarcinoma (10) Urinary tract epithelium: Papillary carcinoma, transitional cell carcinoma, squamous cell carcinoma (11) Placenta epithelium: Choriocarcinoma (12) Testicular epithelium (germ cells): Seminoma, embryonal carcinoma.

Further, tumors derived from more than one neoplastic cells types or derived from more than one germ layers are also treatable.

In a preferred embodiment, the neoplasm to be treated is a solid tumor. More preferably, the size of the solid tumor is larger than $10^8$ cells. Most preferably, the size of the solid tumor is from about $5\times10^9$ to about $10^{11}$ cells.

In a preferred embodiment, the dosage and time to be used for treatment is variable from 1 mg to 50 mg of this conjugated complex for two to six weeks as one course therapy, which can be repeated as needs for achieving a therapeutic benefit.

The following EXAMPLES are presented in order to more fully illustrate the preferred embodiments of the invention. These EXAMPLES should in no way be construed as limiting the scope of the invention, as defined by the appended claims.

EXAMPLES

The present invention is further illustrated by the following examples, which should not be construed as limiting in any way.

Example 1

Methylene diphosphonate (MDP) 100 mg, Ara-C 50 mg and hapten DNP 0.5 mg were added into in stannous chloride 0.05 mg solution, mix and incubate 5 minutes and produced a conjugated as complex. We used thin layer chorography (TLC) analysis the rate of conjugate, drop of the mixture to the beginning of plate of TLC separation on a precoated silica gel plate, dried and develop this plate with benzene acetone (36:13) as a developer, we found the complex by UV light, when the complex reach to top of plate, we only see the complex as one line band, no other bands can be found; on the control TLC, we found three band on the top of plate of TLC. This study showed that MDP, Ara-C and hapten were conjugated as complex with non-covalent reaction by stannous chloride action. The theory of conjugate is not clear; it is used for label isotope Technetium 99 with targeting compound in nuclear medicine for many years. It is our first time to label two or more chemical drugs including targeting compound, chemical drug and hapten for targeting therapy by intravenous administration.

Example 2

Osteosarcoma cell line growth in the culture for days to reach $10\times10^3$ then it is implanted into right arm of mice C57, wait about one week, tumor grow to 1 cm size. We prepared that Methylene Diphosphonate (MDP) 100 mg, Ara-C 50 mg and hapten DNP 0.5 mg were added into the stannous chloride 0.05 mg solution for mixture, incubate 5 minutes and produced a conjugated as complex. For treatment group: iv injection of this conjugated solution in 0.2 ml, two time/week for three weeks, for control group: iv injection of only 0.2 ml Ara-C, two time/week for three weeks. Result: in the treatment group, tumor sizes are smaller than control group's tumor size (P<0.05). Surgical removed tumor for immunological pathological analysis, CD4 and CD8 show positive for MDP-Ara-C-DNP conjugated therapy group, control group show negative of CD4 and CD8. This study showed that this target agent MDP could delivery the complex to the target area like tumor by conjugate formulation with anticancer drugs and hapten, while anticancer drug kill tumor cells and hapten DNP modifying the lysis of tumor to be the stronger antigen to immunological system.

Example 3

Lymphoma cells line growth in the culture for days to reach about $10 \times 10^{3}$, then it is implanted into the right arm of mice C57, about one week, tumor grow to 1 cm size. We prepared that Bruceantin 5 ml, Adymicine 10 mg and hapten DNP 0.5 mg were added into the stannous chloride 0.05 mg solution for mixure incubate 5 minutes and produced a conjugated as complex. For treatment group: iv injection of this conjugated solution in 0.2 ml, two-time/week fro three weeks, for control group: iv injection of only 0.2 ml Ara-C, two-time/week for three weeks. Result: Tumor sizes in the treatment group are smaller than control group's tumor size (P<0.05) Surgical removed tumor for immunological pathological analysis, CD4 and CD8 showed positive for Bruceantin-Adymicine-DNP conjugated treatment group, control group show negative of CD4 and CD8, CytoxiLux analysis showed index of D4 and CD8 antibodies activity is 40% compared with 28% in control group. Also it is found that weight of lymph nodes in treatment group is higher than control group lymph nodes. This study showed that this targeting compound like Bruceantin could delivery a complex to the target area like tumor by conjugate formulation with adymicine with hapten DNP and while anticancer drug kill tumor cells and hapten DNP modifying the lysis of tumor to be stronger antigen to immunological system, function as like tumor cell vaccine.

Example 4

Treatment of Osteocarcinoma, in Combination with Chemotherapy and Topical Therapy One patient, 68 years old, Beijing, China.

Diagnosis: Diagnosis: osteosarcoma in sacroiliac region, diffuse metastasis in both lungs, systemic multiple osseous metastasis The patient admitted into hospital had an obvious pain in the lumbosacral area of left lower limb, adynamic urination and defecation, anepithymia, passive right arm recumbent, and limited motion of both lower limbs. Also Chest and sacral area CT showed diffuse circle-like nodular focus with different sizes in both lungs, the larger is about 2.0 cm, pleural fluid at right side, the iliac sclerotin to the left of sacrum was destructed, and filled with soft tissue.

After admission, a pain alleviation was administered, supported by nutrient heteropathy, the patient was administered slow release depot intratumoral treatment at the sacroiliac region for 9 times, in which the lateral lump at the left iliac was injected for 3 times (the lump in sacral area was injected together), post-CT showed obvious decrease in the lump. During the last two injections of drugs, the patient had lateral radiated pain in sacral area and left lower limb.

Targeting therapy formulation as: Methylene diphosphonate plus Ara-C 50 mg and comprising stannous chloride, mixed for standing 1 minutes, it was conjugated for a complex then were administered intravenous and this treatment were repeated for 6 times; sodium pyrophosphate stannous chloride plus Epirubicin (EPI) 40 mg) were added together for mixture as conjugate, then it was administered intravenous and this therapy was repeated for 6 times, supported by rhG-CSF during the interval of treatments, no adverse effect. Bone scan showed sacral tumor and bone metastasis tumor were smaller than before, the chest and sacroiliac region CT got smaller than before obviously, the general condition of the patient was good, appetite and sleep were better, urination and defecation were normal, the patient could ambulate without support, had no obvious pain. The patient got improvement obviously and discharged on four months of hospitalization.

The patient was admitted the second time on two month later after discharged at of hospital. The chest and sacroiliac region CT showed no obvious change comparison with the last time CT at discharge. After admission, methylene diphosphonate (MDP) with stannous chloride added into Ara-C 50 mg and mixed for conjugated as complex, was administered intravenous for therapy and methylene diphosphonate 20 mg with stannous chloride was added into Ara-C 50 mg and mixed for a conjugate as complex for intravenous therapy fro 4 times, sodium pyrophosphate 10 mg with stannous chloride was added into DDP 20 mg and mixed for a conjugated as complex for intravenous therapy fro 2 times. Patient was getting improvement obviously.

Example 5

Treatment of Gastric and Liver Cancers, in Combination with Topical Treatment

Mr. XXX, 57 years old, a clerk in a company based in Beijing

This patient was admitted first time, because of "abdominal distention and acid reflux for more than 2 months, gastric cancer has been found during the repair of gastric perforation for more than 20 days", He was incapable of ambulation, was raised into the hospital.

Admission diagnosis: gastric antrum cancer at IV stage T4NxM1, metastasis to the lymph node in abdominal cavity, dropsy in the thoracic cavity, wound was not healed after the gastric perforation operation. After admission, anti-cancer Chinese Medicine was orally administered, supported by nutrient, dressings at the incision of operation in the abdominal region (5-Fu,) was changed, the wound was healed at the month later, The lateral lump by the lesser curvature of gastric antrum was administered a intratumoral chemotherapy for 3 times/week for three weeks, the lump at the head of pancreas region was administered intratumoral chemotherapy for 2 times/week fro two weeks, abdominal cavity was perfused for 6 times, in which 5-Fu+DDP 20 mg+IL-2 $10^6$u were administered for 2 times, Bruceantin plus Adriamycin were perfused to abdominal cavity for 4 times in three weeks.

Patient's B ultrasonotrophy showed intrahepatic occupancy, portal vein thrombosis. The patient was suspected of metastasis tumor, but primary hepatic carcinoma was not excluded, because AFP was detected before admission as 1676.3 ng/ml. The intrahepatic lump was administered intratumoral chemotherapy for once. Targeting therapy formulation as sodium phytate as targeting agent in combination with anticancer drugs was administered for 6 times, {the formulated medicament mainly comprises: Ara-C 50 mg was added into DDP 20 mg with stannous chloride and mixed as complex for intravenous drops therapy for a course in 4 weeks, 5-Fu replaced for Ara-C repeated as same as procedure for same intravenous therapy for two courses. ETIFENIN (EHIDA) as target agent in combination with anticancer drugs plus stannous chloride were mixed for a conjugate as a complex, then it was administered intravenous for target therapy and repeated same therapy for 6 times (the formulated medicament mainly comprises: DDP 20 mg for 2 times, 5-Fu 0.5 for 2 times, Ara-C 25 mg for 2 times). The patient had abdominal pain, abdominal distention, decreased appetite, accompanied by night sweating and debilitation, after sodium phytate and ETIFENIN (EHIDA) as target agent in combination with medicament treatment. Heteropathic treatment alleviated the symptoms.

The patient discharged out of hospital on months later, with increased appetite, hepatic function was normal, general condition was better off, B ultrasonotrophy and CT showed the lumps at lesser curvature of gastric antrum and at the head of pancreas region shrank obviously.

Example 6

Treatment of Ovarian Carcinoma

One 56-year-old female ovarian carcinoma patient had a surgical removed the mass 8 years ago. The patient had a big mass in the lower abdomen before the treatment. Sonic-imaging showed a 5×4.1×3 cm size. The patient received couple of courses of chemotherapy that resulted in tumor growth. The patient was administered a target therapy of intravenous of stannous sodium Dimercaptosuccinate (DMS) as target agent for liver tumor in combination with anti-cancer drugs and a intravenous treatment of Tetrofosmin as target agent for liver tumor in combination with anti-cancer drugs. Two weeks later, tumor size reduced to 3.4×3.5×2 cm. The patient has been feeling better and has normal blood cell counts.

Example 7

Malignant Lymphoma

One patient, male, 57 years old, the B ultrasonotrophy in the health checkup on September of 2002 showed: multiple intumescent lymph nodes were present around pancreas in the upper abdomen. Gastroscopy showed mucosal ulcer and multiple nodes, biopsy pathology showed: diffuse non-Hodgkin lymphoma, small cell type. On November of 2002, axillary lymph node was biopsied, pathology showed NHL small cell type, CD20 (+). From November of 2002 to August of 2003, the radiotherapy at both axillary regions was administered with DT49Gy, the radiotherapy at both neck regions were administered with DT45Gy. After radiotherapy, the chest CT showed: left axillary lymph node was the same size as before. Regular re-examinations were carried on afterwards, the CT on January of 2005 showed: the lump under the right diaphragmatic muscle was 11.0×11.3 cm. After the admission to the Chinese Academy of Medical Sciences on November, the biopsy pathology showed: the lump under the right diaphragmatic muscle was non-Hodgkin lymphoma, small cleaved cell, morphology and immunohistochemistry supported hat band area lymphoma CD20 (+). Chemotherapy of DDP (40 mg/day 1-3) Vp-16 0.1 mg/day 1-3 IFO (with cyclophosphamide) 2.0/day 2-4 was administered, the bone marrow was inhibited to the III degree after the chemotherapy. The re-examination CT followed a period of two-week chemotherapy showed: the irregular lump of soft tissue at the right posterior pleural membrane and posterior to crura of diaphragm shrank, the largest cross-section was 8.5×3.2 cm, the low density shadow posterior to the inferior caval vein was the same as before and suspected of invasion, multiple nodus were present in abdominal cavity, posterior to peritoneal membrane and anterior to sacrum, multiple lymph nodes were present in the right inguinal groove, middle amount of hydrops were in the thoracic cavity. The hydrops was drawn off by puncture from the right thoracic cavity, cytology reported: a large amount of lymphocytes and mesothelial cells. The patient was admitted to the hospital for further treatment.

The B ultrasonotrophy on Feb. 11, 2006 showed: size and morphology of liver were normal, a solid low-echo node in the size of 4.5×1.8 cm was detected at the left lobe of liver, with irregular morphology, with clear boundary, symmetric echo inside, a size of about 1.1×1.0 cm cystic echo was detected in the right lobe of liver, the rest of liver had solid symmetric echo, the direction of blood vessels were clear and regular, portal vein was not dilated; multiple solid low-echo nodus were detected by the side of blood vessels in the abdominal cavity, the larger is the size of 1.5×0.8 cm, a diffuse thickening of part of the small intestine wall was detected in the right lower abdomen (to the right of hylum), the thickest thickness was about 1.2 cm; a solid low-echo area in a range of about 6.5×4.4×1.9 cm was detected at the posterior inferior angle of right diaphragm, with clear boundary and symmetric echo.

After the intravenous target therapy of Bruceantin, Tetrandrine, thalicarpine, maytansine seperately as target agents in combination with anti-cancer drugs by stannous chloride affection for a conjugate as complex for six courses (all kinds of anti-cancer drugs), the effect was obvious.

The B ultrasonotrophy on Feb. 22, 2006 showed: the thickened part of small intestine in the right lower abdomen was obviously limited than before, the thickness of the wall was about 1.1 cm.

From Feb. 27, 2006 to Mar. 24, 2006, the intravenous target chemotherapy of Bruceantin and Tetrandrine separately as target agents in combination with anti-cancer drugs by stannous chloride effective for conjugate as complex was administered for a period of four week. On Mar. 25, 2006, the color Doppler ultrasonic re-examination in Shandong Medical Imaging Research Institute reported: the size and morphology of liver were normal, a cystic opaque area of about 1.7×1.3 cm was detected in the right posterior lobe; a low-echo nodus of 1.6×1.3 cm was detected in the left lobe, with clear boundary and symmetric echo inside; portal vein, intrahepatic and extrahepatic bile ducts were not dilated; bile, pancreas, spleen and both kidneys were normal; post-peritoneal membrane scanning showed: a low-echo nodus of 0.5× 0.7 cm was detected above the pancreas body, in a regular shape; an irregular aqueous opaque area in a range of about 5.4×3.8 cm was detected in the right thoracic cavity, the pleural membranes was thickened at the crus of diaphragm of right ribs, the most thickness was about 1.1 cm, a solid low-echo in a range of about 2.8×1.2×2.6 cm was detected in the posterior inferior angle of right diaphragm, with clear boundary and symmetric echo.

The intravenous target chemotherapy of Bruceantin as targeting compound in combination with anti-cancer drugs by stannous chloride function for conjugate as complex was continued for several courses. The CT re-examination in Shandong Medical Imaging Research Institute on Jul. 3, 2006 reported: re-examination of post-peritoneal membrane lymphoma: the focus between right inferior caval vein and crus of diaphragm disappeared, the focus on the right posterior abdominal wall essentially disappeared, the diaphragmatic muscle at the same side were still thickened, patchy, cord high-density shadow were seen in the apical segment of superior lobe of right lung and the posterior segment of superior lobe of left lung, the right pleural membrane was thickened topically and adhered partially, bronchia were smooth, no stenosis in the lumen, no abnormal growed lymph node was seen at the hilum of lung and in the mediastinum. The lump of soft tissue interior to the internal iliac intramuscle at the interior wall of right pelvic cavity shrank than before.

During the hospitalization, the patient was administered Bruceantin as targeting compound, in combination with the medicaments of 16 times (Arsenic trioxide 5 mg) and 6 times (Ara-C 50 mg), 12 times (cyclophosphamide 0.1), 2 times and VP 16) 50 mg.

Example 8

Treatment for Pancreatic Cancer

One patient, female, 68 years old, had pancreatic tumor with invasion of aorta vein. KPS score was 70 and sonicimaging showed tumor size of 4.6×5.3 cm with an irregular ball shape. Clinical diagnosis was pancreas carcinoma in II stage, T3N1M0.

She received intravenous target therapy of NOET as target agent in combination with a composition containing stannous chloride, hapten (DNP) and anticancer drug Ara-C, and mixed for a conjugate as complex. After four weeks, tumor shrank to 3.7×4.5 cm. The patient was in very good condition with normal blood cell counts.

Example 9

Treating Renal Carcinoma

One patient, male, 68 years old, was diagnosed by X-ray as having a renal carcinoma, pathologically diagnosed as having a renal cell carcinoma, having a tumor with the size of 1.5×2 cm. The patient was administered a intravenous target therapy of Pentetic Acid with Stannous Chloride (DTPA) and Sodium Dimercaptosuccinate (DMSA-V) as target agent in combination with anti-cancer drugs, the composition comprising Haptens and anti-cancer drug Ara-C then mixed as conjugate as complex. Two weeks later, the patient has been feeling better. Three weeks later, the tumor disappeared. The patient was in very good condition with normal blood cell counts.

Example 10

Treating Brain Carcinoma

One patient, male, 58 years old, had an encephaloma, astrocytoma in V grade. CT showed a 3×4 cm tumor in the right frontal lobe. His general condition was general. He had been administered a chemotherapy for 5 times, but the effect was poor. Therefore, he came to our hospital to receive an intravenous target treatment. The patient was administered a intravenous target treatment of L, L-Ethyl Cysteinate Dimer with Stannous Chloride (ECD) and Stannous Exametazime separately as target agents in combination with anti-cancer drug (ARA-C), mixed for a conjugate as complex, was administered, followed a intravenous target treatment of L,L-Ethyl Cysteinate Dimer with Stannous Chloride (ECD) as target in combination with Adriamycin, mixed for a conjugate as complex, was administered; an a intravenous target treatment of Stannous Exametazime with stnnous chloride as target agent in combination with CTX and MTX for a conjugate as complex for 4 times. The effect was very good, with the tumor shrank apparently. CT showed that the size of the tumor was 1×1.5 cm.

Since modifications will be apparent to those of skill in this art, it is intended that this invention be limited only by the scope of the appended claims.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

What is claimed is:

1. A conjugated complex, comprising:
   a targeting compound; and
   a chemical drug;
   wherein said targeting compound is non-covalently complexed to said chemical drug via a redox agent as a reactant.

2. The conjugated complex of claim 1, wherein the redox agent is selected from the group consisting of stannous chloride ($SnCl_2$), stannous sulfate ($SnSO_3$), stannous oxide (SnO), stannic oxide ($SnO_2$), sodium stannate ($Na_2SnO_3$), sodium stannite ($Na_2SnO_2$), stannic chloride ($SnCl_4$), thiostannate ($SnS_3$), and stannous sulfide (SnS).

3. The conjugated complex of claim 1, wherein said targeting compound is selected from the group consisting of a carrier capable of delivering an agent to a targeted tissue, Sodium Dimercaptosuccinate (III) (DMSA-III), Sodium Dimercaptosuccinate (V) (DMSA-V), Sodium Pyrophosphate and Stannous Chloride for Injection (PYP), Methylene Diphosphonate for Injection (MDP), polymerized albumin, Mercaptoacetyltriglycine, Pentetic Acid and Stannous Chloride (DTPA), Sodium Glucoheptonate and Stannous Chloride, L,L-Ethyl Cysteinate Dimer and Stannous Chloride (ECD), Exametazime (HMPAO), Etifenin and Stannous Chloride, Sodium Phytate and Stannous Chloride, $Cu(MIBI)_4BF_4$ (MIBI), α-methyltyrosine, MIBI (2-methoxy isobutyl isonitrile), 2-nitroimidazole, monoclonal antibodies and monoclonal antibodies against neoplasm, and a traditional Chinese drug extract selected from the group consisting of Bruceantin, Tetrandrine, thalicarpine and maytansine.

4. The conjugated complex of claim 3, wherein said chemical drug is selected from the group consisting of cisplatin, carboplatin, calcium folinate, vincristine, methotrexate, fluorouracil, cytosine arabinoside (Ara-C), cyclophosphamide, epirubicin, doxorubicin rapid dissolution, mitomycin, etoposide, bleomycin A5.

5. The conjugated complex of claim 1, wherein said chemical drug is selected from the group consisting of cisplatin, carboplatin, calcium folinate, vincristine, methotrexate, fluorouracil, cytosine arabinoside (Ara-C), cyclophosphamide, epirubicin, doxorubicin rapid dissolution, mitomycin, etoposide, bleomycin A5.

6. The conjugated complex of claim 1, further comprising an anti-neoplasm agent.

7. The conjugated complex of claim 6, wherein the anti-neoplasm agent is selected from the group consisting of an alkylating agent, an antimetabolite, a natural product, a platinum coordination complex, an anthracenedione, a substituted urea, a methylhydrazine derivative, an adrenocortical suppressant, a hormone, an antagonist, an anti-cancer polysaccharide, an herb extract and a traditional Chinese drug extract.

8. The conjugated complex of claim 1, further comprising an immune response potentiator.

9. The conjugated complex of claim 8, wherein the immune response potentiator is selected from the group consisting of Bacille Calmette-Guerin (BCG), *Corynebacterium Parvum*, *Brucella abortus*, glucan, levamisole, tilorone, an enzyme and a nonvirulent virus.

10. The conjugated complex of claim 1, wherein the redox agent is $SnCl_2$ and the targeting compound is an organ- or neoplasm-targeting compound.

11. The conjugated complex of claim 1, wherein the redox agent is $SnCl_2$ and the chemical drug is a compound having anticancer effects.

12. The conjugated complex of claim 1, wherein the redox agent is from about 0.01% (w/w) to about 35% (w/w), the targeting compound is from about 1% (w/w) to about 98% (w/w), and the chemical drug is from about 1 mg/ml to about 80 mg/ml.

13. A kit comprising the conjugated complex of claim 1.

14. An article of manufacture, comprising:
 a) packaging material;
 b) the conjugated complex of claim 1; and
 c) a label indicating that the article is for treating neoplasms.

15. The conjugated complex of claim 1, wherein said chemical drug is a chemotherapeutic agent.

16. A conjugated complex, comprising:
 a targeting compound; and
 a chemical drug;
 wherein said targeting compound is non-covalently complexed to said chemical drug.

* * * * *

UNITED STATES PATENT AND TRADEMARK OFFICE
CERTIFICATE OF CORRECTION

Page 1 of 3

PATENT NO. : 8,501,243 B2
APPLICATION NO. : 12/440198
DATED : August 6, 2013
INVENTOR(S) : Yu It is certified that error appears in the above-identified patent and that said Letters Patent is hereby corrected as shown below:

On the Title Page

In column 2 (page 1 item 56) at line 6, Under Other Publications, change "Angiogensis" to --Angiogenesis--.

In column 2 (page 1 item 56) at line 15, Under Other Publications, change "Paraetamol" to --Paracetamol--.

In column 2 (page 1 item 56) at line 31, Under Other Publications, change "Otolaryngol" to --Otolaryngology--.

In column 2 (page 1 item 56) at line 37, Under Other Publications, change "trails" to --trials--.

In column 2 (page 1 item 56) at line 52, Under Other Publications, change "Macrophase" to --Macrophage--.

In column 1 (page 2 item 56) at line 14, Under Other Publications, change "angiogensis" to --angiogenesis--.

In column 2 (page 2 item 56) at line 31, Under Other Publications, change "Invormaiton," to --Information,--.

In the Specification

In column 3 at lines 28-29, Change "desintegration" to --disintegration--.

In column 4 at line 22, Change "bruccal," to --buccal,--.

In column 7 at line 12, Change "gallblader" to --gallbladder--.

In column 7 at line 23, Change "(N-e-diethylenetriaminepetaacetic acid)" to --(N-e-diethylenetriaminepentaacetic acid)--.

In column 7 at lines 25-26, Change "carbodimide." to --carbodiimide.--.

In column 7 at line 46, Change "adminstered" to --administered--.

Signed and Sealed this
Eighteenth Day of March, 2014

Michelle K. Lee
*Deputy Director of the United States Patent and Trademark Office*

CERTIFICATE OF CORRECTION (continued)
U.S. Pat. No. 8,501,243 B2

In column 7 at line 67, Change "injection" to --injection.--.

In column 10 at line 39, Change "carbodimide." to --carbodiimide.--.

In column 11 at lines 48-49, Change "(N-e-diethylenetriaminepetaacetic acid)" to --(N-e-diethylenetriaminepentaacetic acid)--.

In column 11 at line 52, Change "carbodimide." to --carbodiimide.--.

In column 11 at line 63, Change "13-Gal" to --β-Gal--.

In column 12 at line 36, Change "metastastic," to --metastatic,--.

In column 12 at line 62, Change "MODES FOR" to --MODES OF--.

In column 16 at line 3, Change "endotheliase"" to --endothelial"--.

In column 16 at line 14 (approx.), Change "polypospis coli)." to --polyposis coli).--.

In column 22 at line 18, Change "a-methyltyosine;" to --α-methyltyrosine;--.

In column 22 at line 30, Change "Ovabulin" to --Ovalbumin--.

In column 22 (Table 3) at line 12, Change "Steriods" to --Steroids--.

In column 22 (Table 3) at line 13, Change "medroxyprogeste-rone," to --medroxyprogesterone,--.

In columns 23-24 (Table 3-continued) at line 12, Change "protanine," to --protamine,--.

In columns 23-24 (Table 3-continued) at line 39, Change "herbamycin," to --herbimycin,--.

In columns 23-24 (Table 3-continued) at line 55, Change "interfereons," to --interferons,--.

In columns 23-24 (Table 3-continued) at line 59, Change "steriods" to --steroids--.

In columns 25-26 (Table 3-continued) at line 10, Change "Scolecobasiwn" to --Scolecobasidium--.

In column 25 at line 56, Change "carboxyamido-trizole" to --carboxyamido-triazole--.

In column 25 at line 58, Change "cortisone/hyaluroflan," to --cortisone/hyaluronan,--.

In column 25 at line 65, Change "beta-cyclodextran," to --beta-cyclodextrin,--.

In column 26 at lines 62-63, Change "tetrahydrocortisol-sthrombospondins (TSPs)," to --tetrahydrocortisol-thrombospondins (TSPs),--.

In column 27 at line 5, Change "angiostain, endostain," to --angiostatin, endostatin,--.

In columns 27-28 (Table 4) at line 19, Change "Hexamethyhnelanine" to --Hexamethylmelamine--.

In columns 27-28 (Table 4) at line 21, Change "Alkly" to --Alkyl--.

In columns 27-28 (Table 4) at line 42, Change "Fluorouacil" to --Fluorouracil--.

In columns 29-30 (Table 4-continued) at line 8, Change "Wihns'tumor," to --Wilms' tumor,--.

In columns 29-30 (Table 4-continued) at line 18, Change "rhab-domyosarcoma," to --rhabdomyosarcoma,--.

CERTIFICATE OF CORRECTION (continued)

U.S. Pat. No. 8,501,243 B2

In columns 29-30 (Table 4-continued) at lines 62-63 (approx.), Change "Adrenocortico-steriods" to --Adrenocortical-steroids--.

In columns 29-30 (Table 4-continued) at line 71, Change "Medroxyprogestrone" to --Medroxyprogesterone--.

In column 31 at lines 63-64, Change "carbodimide." to --carbodiimide.--.

In column 33 at lines 42-43, Change "(N-e-diethylenetri-aminepetaacetic acid)" to --(N-e-diethylenetriaminepentaacetic acid)--.

In column 34 at line 16, Change "α-methyltyosine," to --α-methyltyrosine,--.

In column 34 at line 36, Change "TNF-ot," to --TNF-α,--.

In column 34 at line 38, Change "carboxyamido-trizole" to --carboxyamido-triazole--.

In column 34 at line 40, Change "cortisone/hyaluroflan," to --cortisone/hyaluronan,--.

In column 34 at line 47, Change "beta-cyclodextran," to --beta-cyclodextrin,--.

In column 34 at lines 61-62, Change "tetrahydrocortisol-sthrombospondins (TSPs)," to --tetrahydrocortisol-thrombospondins (TSPs),--.

In column 35 at lines 2-3, Change "angiostain, endostain," to --angiostatin, endostatin,--.

In column 35 at line 43, Change "bruccal," to --buccal,--.

In column 35 at lines 55-56, Change "colonrectal cancer," to --colorectal cancer,--.

In column 36 at lines 14-15, Change "chlangiocarcinoma" to --cholangiocarcinoma--.

In column 37 at line 29, Change "fro" to --for--.

In column 37 at line 41, Change "delivery" to --deliver--.

In column 38 at line 30, Change "fro" to --for--.

In column 38 at line 33, Change "fro" to --for--.

In column 38 at line 60, Change "fro" to --for--.

In column 38 at line 64, Change "B ultrasonotrophy" to --B ultrasonography--.

In column 39 at line 23, Change "B ultrasonotrophy" to --B ultrasonography--.

In column 39 at line 48, Change "B ultrasonotrophy" to --B ultrasonography--.

In column 40 at line 18, Change "B ultrasonotrophy" to --B ultrasonography--.

In column 40 at line 39, Change "B ultrasonotrophy" to --B ultrasonography--.

In column 42 at line 4, Change "an a" to --and a--.